United States Patent
Wallace-Davis et al.

(10) Patent No.: US 8,187,453 B2
(45) Date of Patent: May 29, 2012

(54) TRIGLYCERIDE AND CHOLESTEROL SENSING METHOD AND SENSOR

(75) Inventors: Emma Naomi Kathleen Wallace-Davis, Oxfordshire (GB); Lindy Jane Murphy, Oxfordshire (GB); Andrew William Allan, Oxfordshire (GB)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/973,205

(22) Filed: Dec. 20, 2010

(65) Prior Publication Data

US 2011/0086373 A1 Apr. 14, 2011

Related U.S. Application Data

(62) Division of application No. 12/097,364, filed as application No. PCT/GB2006/004848 on Dec. 21, 2006, now abandoned.

(30) Foreign Application Priority Data

Dec. 21, 2005 (GB) .................................. 0526051.8

(51) Int. Cl.
*G01N 27/327* (2006.01)

(52) U.S. Cl. ........... 205/777.5; 204/403.03; 204/403.04; 205/792

(58) Field of Classification Search .......... 204/403.01–403.15; 205/777.5, 205/778, 792
See application file for complete search history.

(56) References Cited

U.S. PATENT DOCUMENTS

| | | | |
|---|---|---|---|
| 4,045,297 A | 8/1977 | Weeks et al. | |
| 5,126,245 A | 6/1992 | Motoyama et al. | |
| 5,236,567 A * | 8/1993 | Nanba et al. | 204/403.1 |
| 5,288,636 A * | 2/1994 | Pollmann et al. | 204/403.14 |
| 5,780,256 A | 7/1998 | Ueda et al. | |
| 5,856,156 A | 1/1999 | Ambrosius et al. | |
| 6,071,392 A | 6/2000 | Yamamoto et al. | |
| 6,214,612 B1 | 4/2001 | Yamamoto et al. | |
| 2005/0003523 A1 | 1/2005 | Anaokar et al. | |
| 2005/0164329 A1 | 7/2005 | Wallace-Davis et al. | |
| 2005/0214891 A1 | 9/2005 | Horn et al. | |
| 2010/0140108 A1 * | 6/2010 | Roblin et al. | 205/775 |

FOREIGN PATENT DOCUMENTS

| | | |
|---|---|---|
| EP | 0125867 A2 | 11/1984 |
| EP | 0230786 A1 | 8/1987 |
| EP | 0709456 A2 | 5/1996 |
| EP | 0794429 A1 | 9/1997 |
| EP | 1150118 A1 | 10/2001 |
| EP | 1482307 A1 | 12/2004 |
| EP | 1555326 A1 | 7/2005 |
| EP | 1873516 A1 | 1/2008 |
| JP | 11-051896 | 2/1999 |

(Continued)

OTHER PUBLICATIONS

Winartasaputra, et al., "Amperometric Enzymic Determination of Triglycerides in Serum," Anal. Chem. 1982, 54, 1987-1990.

(Continued)

*Primary Examiner* — Alex Noguerola
(74) *Attorney, Agent, or Firm* — Quarles & Brady LLP; George E. Haas

(57) ABSTRACT

A method for the determination of the amount of cholesterol in a sample is provided. The method typically provides a breakdown of the HDL and LDL cholesterol contents of the sample.

20 Claims, 14 Drawing Sheets

FOREIGN PATENT DOCUMENTS

| WO | 00/73797 | A2 | 12/2000 |
|---|---|---|---|
| WO | 03/056319 | A2 | 7/2003 |
| WO | 03/097860 | A1 | 11/2003 |
| WO | 03/097864 | A1 | 11/2003 |
| WO | 20061000828 | A2 | 1/2006 |
| WO | 20061000829 | A2 | 1/2006 |
| WO | 20061067424 | A1 | 6/2006 |

OTHER PUBLICATIONS

Laurinavicius, et al., "Amperometric Glyceride Biosensor," Analytic. Chimica Acta 330 (1996) 159-166.

International Search Report, PCT/GB2006/004848, mail date Jun. 7, 2007.

Johannes Everse, et al.; The Pyridine Nucleotide Ceonzymes; 1982; Academic Press.

Klingenberg, Martin, "Nicotinamide-adenine Dinucleotides and Dinucleotide Phosphates (NAD, NADP, NASDH, NADPH)", Methods of Enzymatic Analysis, pp. 251-284, Verlag Chemie (1985).

Feldbrugge, et al, "Development and practical evaluation of an amperometric triglyceride sensor"; Sensors and Actuators B; vol. 19; pp. 365-367 (1994).

* cited by examiner

TRIGLYCERIDE AND CHOLESTEROL SENSING METHOD AND SENSOR

CROSS-REFERENCE TO RELATED APPLICATIONS

This application is a division of U.S. patent application Ser. No. 12/097,364 filed on Jun. 13, 2008, now abandoned, which claimed benefit under 35 U.S.C. §371 of International patent application number PCT/GB2006/004848 filed on Dec. 21, 2006, that in turn claimed priority under 35 U.S.C. §119 of United Kingdom patent application number 0526051.8 filed on Dec. 21, 2005.

STATEMENT REGARDING FEDERALLY SPONSORED RESEARCH OR DEVELOPMENT

Not Applicable

FIELD OF THE INVENTION

The present invention relates to methods for determining the amount of cholesterol in a sample. The invention also relates to reagent mixtures and a kit for use in such methods.

BACKGROUND TO THE INVENTION

In the current climate of increasing incidence of disorders related to high cholesterol, in particular coronary artery disease (CAD), there is an increasing demand for effective cholesterol testing. Many epidemiological investigations have demonstrated the strong and independent inverse association of high density lipoprotein (HDL), measured in terms of either its cholesterol or apo A1 content, to risk of CAD. It is said that the risk of CAD increases 2-3% for every 10 mg/L decrease in HDL-cholesterol. Thus, higher HDL-cholesterol concentrations are considered protective. Conversely, higher concentrations of low density lipoproteins (LDL) are considered to have an adverse effect. Therefore, cholesterol tests should preferably not only indicate the total cholesterol levels, but also provide a measurement of the LDL cholesterol and HDL cholesterol levels.

The test procedures currently available to clinicians generally require a sample to be sent away to a laboratory test facility for such results to be obtained. This causes an undesirable time delay between test samples being taken from a patient and a diagnosis being reached. There is therefore a need for simple, effective and rapid methods for analysing the cholesterol content of body fluids such as blood or plasma, in particular methods that can provide results at the point of care. Preferred methods therefore will not employ specialist equipment, or require trained technicians to carry out. Further, any such method should preferably be capable of effectively distinguishing between cholesterol bound to HDL, and cholesterol bound to LDL.

SUMMARY OF THE INVENTION

The present invention provides a method for the determination of the total amount of cholesterol in a sample, the method comprising reacting the sample with a first series of reagents comprising
 (a1) a surfactant comprising one or more bile acid derivatives or salts thereof;
 (b1) a cholesterol ester hydrolysing reagent;
 (c1) cholesterol dehydrogenase;
 (d1) a coenzyme;
 (e1) a redox agent capable of being oxidised or reduced to form a product; and optionally
 (f1) a reductase,
and electrochemically detecting the amount of product formed.

In preferred embodiments, the method of the invention also provides a measurement of the triglyceride content of the sample, as well as the content of cholesterol in the sample, which is bound to high density lipoproteins (HDL cholesterol). From these measurements, the amount of cholesterol bound to low density lipoproteins (LDL cholesterol) can be determined.

The triglyceride content of a sample can be determined by reacting the sample with a second series of reagents comprising
 (a2) a surfactant comprising one or more bile acid derivatives or salts thereof;
 (b2) a triglyceride hydrolysing reagent;
 (c2) glycerol dehydrogenase;
 (d2) a coenzyme;
 (e2) a redox agent capable of being oxidised or reduced to form a product; and optionally
 (f2) a reductase,
and electrochemically detecting the amount of product formed.

For the avoidance of doubt, the references in this specification to "series" of reagents do not require two or more sequential steps. Thus, said first series of reagents can, for example, be a single mixture of reagents, which is typically provided in a single electrochemical well. Similarly, said second series of reagents can be a single mixture of reagents, typically provided in a separate electrochemical well. A further series of reagents may likewise be a single mixture of reagents, typically provided in a further separate electrochemical well.

Thus, the invention provides a simple, electrochemical test for determining cholesterol content, which is also capable of providing an indication of the HDL cholesterol content as well as the LDL cholesterol content of the sample. The electrochemical test requires no particular skill on the part of the user and can therefore be carried out by untrained personnel. Test results are also provided very quickly, typically within a matter of minutes. The invention therefore provides a simple point of care cholesterol test which, for example using only a drop of blood, can provide a rapid but detailed analysis of a patient's cholesterol levels.

The present invention also provides a first reagent mixture for use in an electrochemical method for the determination of the total amount of cholesterol in a sample, the first reagent mixture comprising components (a1) to (e1) and optionally (f1) as set out above. A second reagent mixture for use in an electrochemical method for the determination of the amount of triglyceride in a sample is also provided, the second reagent mixture comprising components (a2) to (e2) and optionally (f2) as set out above.

The present invention also provides use of one or more bile acid derivatives or salts thereof as a surfactant to break down the lipoprotein structure in an electrochemical method for the determination of the total amount of cholesterol in a sample, said method comprising reacting the sample with a first series of reagents comprising components (a1) to (e1) and optionally (f1) as set out above. Use of one or more bile acid derivatives or salts thereof as a surfactant to break down the lipoprotein structure in an electrochemical method for the determination of the amount of triglyceride in a sample is also provided, said method comprising reacting the sample with a second series of reagents comprising components (a2) to (e2) and optionally (f2) as set out above.

Also provided is a kit for measuring the total cholesterol content of a sample, the kit comprising a first and optionally further electrochemical cells, each cell having a working electrode, a reference or pseudo reference electrode and optionally a separate counter electrode;

a first series of reagents as described herein, said first series of reagents being associated with said first electrochemical cell;

a power supply for applying a potential across the or each cell; and a measuring instrument for measuring the resulting electrochemical response of or each cell.

The kit also preferably comprises a second electrochemical cell and a second series of reagents associated with said second electrochemical cell, the second series of reagents providing a measurement of the triglyceride content of the sample. A third electrochemical cell and a third series of reagents associated therewith may also be provided, wherein the third series of reagents is for the determination of the content of HDL cholesterol in the sample.

Also provided is a method of operating a kit of the invention, the method comprising contacting a sample with the reagents of or each electrochemical cell; applying a potential across the or each electrochemical cell; and electrochemically detecting the amount of product formed in the or each electrochemical cell by measuring the resulting electrochemical response.

DETAILED DESCRIPTION OF THE INVENTION

Figure 1:
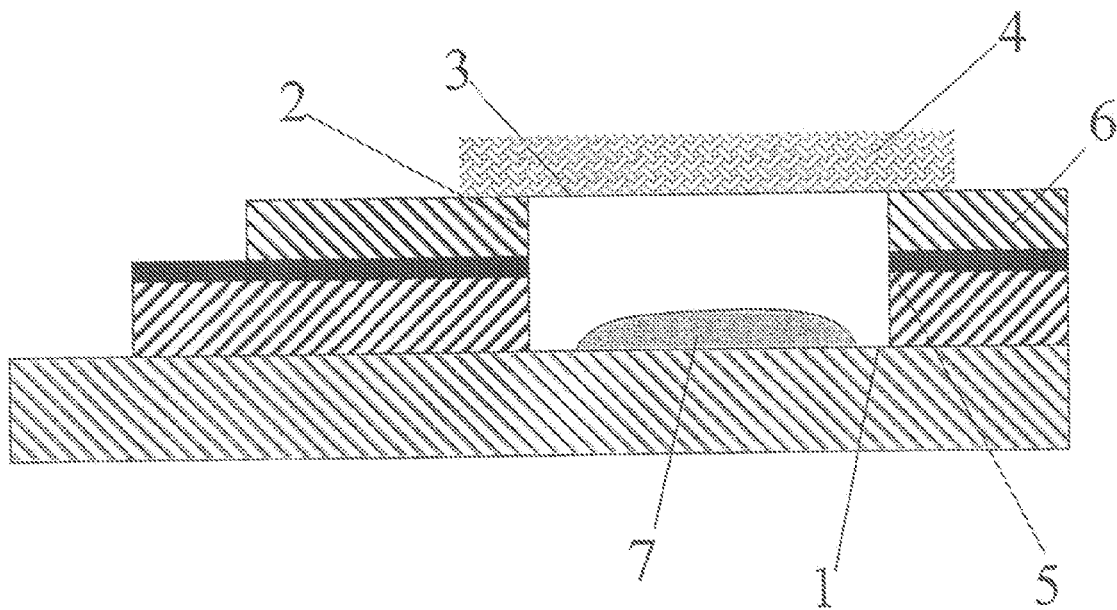
FIG. 1 depicts an electrochemical cell according to one embodiment of the invention.

The present invention provides a method of determining the cholesterol profile of a patient. Typically, the invention provides a test for the total cholesterol content of a sample, and in preferred embodiments, tests for the triglyceride content and the HDL cholesterol contents are also provided. This enables the LDL content of the sample to be calculated using the Friedwald equation.

Total Cholesterol Test

The total cholesterol test involves reacting the sample with a first series of reagents comprising a surfactant, a cholesterol ester hydrolysing reagent, cholesterol dehydrogenase, a coenzyme and a redox agent. A reductase is also preferably used. The mixture of sample and reagents is contacted with a working electrode of an electrochemical cell so that redox reactions occurring can be detected. A potential is applied across the cell and the resulting electrochemical response, typically the current, is measured.

Cholesterol found in the body is bound to lipoproteins. In order to access the cholesterol, and to enable reaction with the remaining assay ingredients, it is therefore necessary to break down the lipoprotein structure using a surfactant. The surfactants employed in the present invention are bile acid derivatives or salts thereof, since these have been found to effectively break down lipoproteins. Examples of suitable bile acid derivatives include cholic acid, taurocholic acid, glycocholic acid, lithocholic acid, deoxycholic acid, CHAPS (3-[(3-cholamidopropyl)-dimethylammonio]propane), CHAPSO, BIGCHAP and deoxy BIGCHAP. Examples of suitable salts include sodium and potassium salts. In particular, sodium taurocholate (NaTC) and potassium taurocholate (KTC) may be mentioned as a preferred salt of a bile acid derivative for use in the present invention.

Combinations of two or more bile acid derivatives or their salts may also be used. For example, use of CHAPS alone has been found to occasionally cause precipitation of the enzymes present. Therefore, a combination of CHAPS with a different surfactant, which does not have this effect, e.g. deoxy BIGCHAP, has been found to be beneficial. In a preferred embodiment, CHAPS and deoxy BIGCHAP are used in a 1:1 ratio.

The total amount of surfactant present is typically from 5 to 200%, from 50 to 160%, from 50 to 100% or from 60 to 85%, preferably from 70 to 80% by weight relative to the weight of the cholesterol dehydrogenase enzyme.

Once the lipoprotein structure has been broken down, cholesterol both in its free form and in the form of cholesterol esters, becomes available for reaction. Since the subsequent assay only tests for free cholesterol, the cholesterol esters are hydrolysed to provide free cholesterol using a cholesterol ester hydrolysing reagent. The cholesterol ester hydrolysing reagent may be any reagent capable of hydrolysing cholesterol esters to cholesterol. The reagent should be one which does not interfere with the reaction of cholesterol with cholesterol dehydrogenase and any subsequent steps in the assay. Preferred cholesterol ester hydrolysing reagents are enzymes, for example cholesterol esterase and lipases. A suitable lipase is, for example, a lipase from a pseudomonas or *chromobacterium viscosum* species. Commercially available enzymes, optionally containing additives such as stabilisers or preservatives may be used, e.g. those available from Toyobo or Amano. The cholesterol ester hydrolysing reagent is typically used in an amount of from 1 to 20%, from 1 to 10%, preferably from 3 to 7% by weight relative to the weight of the cholesterol dehydrogenase enzyme.

The liberated cholesterol is reacted with cholesterol dehydrogenase to provide a reduced form of the cholesterol dehydrogenase in accordance with the assay below.

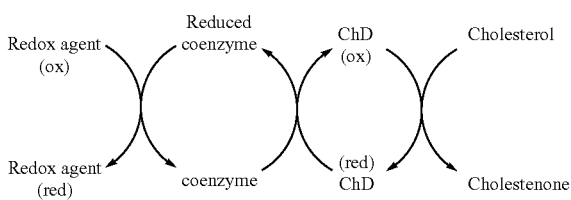

where ChD is cholesterol dehydrogenase. The amount of reduced redox agent produced by the assay is detected electrochemically, thus providing an indication of the total cholesterol content of the sample. Additional reagents may also be included in this assay if appropriate.

Any commercially available form of cholesterol dehydrogenase may be employed. For instance, the cholesterol dehydrogenase may be from the *Nocardia* species. The cholesterol dehydrogenase may be used in an amount of from 0.1 to 60 mg per 100 μl of sample to be tested, from 0.1 to 20 mg per 100 μl, preferably from 0.5 to 10 mg per 100 μl.

An enzyme employed as the cholesterol ester hydrolysing reagent and/or the cholesterol dehydrogenase may contain additives such as stabilisers or preservatives. Further, each of the enzymes may be chemically modified.

Typically the coenzyme is $NAD^+$ or an analogue thereof. An analogue of $NAD^+$ is a compound having structural characteristics in common with $NAD^+$ and which also acts as a coenzyme for cholesterol dehydrogenase. Examples of $NAD^+$ analogues include $APAD^+$ (Acetyl pyridine adenine dinucleotide); $TNAD^+$ (Thio-NAD); $AHD^+$ (acetyl pyridine hypoxanthine dinucleotide); $NaAD^+$ (nicotinic acid adenine dinucleotide); $NHD^+$ (nicotinamide hypoxanthine dinucleotide); and $NGD^+$ (nicotinamide guanine dinucleotide). $TNAD^+$ is a preferred coenzyme as it has been found to provide a better performance in the assay. The coenzyme is typically used in an amount of from 0.5 to 30% by weight or from 5 to 30% by weight relative to the weight of the cholesterol dehydrogenase enzyme. As used herein, $TNAD^+$ refers to Thio-NAD or a salt thereof, such as $TNADK^+$.

Typically, the redox agent should be one, which can be reduced in accordance with the assay shown above. In this case, the redox agent should be one, which is capable of accepting electrons from a coenzyme (or from a reductase as described below) and transferring the electrons to an electrode. The redox agent may be a molecule or an ionic complex. It may be a naturally occurring electron acceptor such as a protein or may be a synthetic molecule. The redox agent will typically have at least two oxidation states.

Preferably, the redox agent is an inorganic complex. The agent may comprise a metallic ion and will preferably have at least two valencies. In particular, the agent may comprise a transition metal ion and preferred transition metal ions include those of cobalt, copper, iron, chromium, manganese, nickel, or ruthenium. The redox agent may be charged, for example it may be cationic or alternatively anionic. An example of a suitable cationic agent is a ruthenium complex such as $Ru(NH_3)_6^{3+}$, an example of a suitable anionic agent is an iron complex such as $Fe(CN)_6^{3-}$ (ferricyanide).

Examples of complexes which may be used include $Cu(EDTA)^{2-}$, $Fe(CN)_6^{3-}$, $Fe(CN)_5(O_2CR)^{3-}$, $Fe(CN)_4(oxalate)^{3-}$, $Ru(NH_3)_6^{3+}$ and chelating amine ligand derivatives thereof (such as ethylenediamine), $Ru(NH_3)_5(py)^{3+}$, $Ru(acac)_2(Py-3-CO_2H)(Py-3-CO_2)$, ferrocenium and derivatives thereof with one or more of groups such as $—NH_2$, $—NHR$, $—NHC(O)R$, and $—CO_2H$ substituted into one or both of the two cyclopentadienyl rings. Preferably the inorganic complex is $Fe(CN)_6^{3-}$, $Ru(NH_3)_6^{3+}$, $Ru(NH_3)_5(py)^{3+}$, $Ru(acac)_2(Py-3-CO_2H)(Py-3-CO_2)$, or ferrocenium monocarboxylic acid (FMCA). The redox agent is typically used in an amount of from 1 to 60%, from 5 to 60%, preferably from 20 to 60%, from 30 to 60%, preferably from 40 to 60% by weight relative to the weight of the cholesterol dehydrogenase enzyme.

In a preferred embodiment, the reagent mixture used in the electrochemical assay additionally comprises a reductase. The reductase typically transfers two electrons from the reduced NAD and transfers two electrons to the redox agent. The use of a reductase therefore provides swift electron transfer. The reductase may also encourage the reaction to occur more quickly.

Examples of reductases which can be used include diaphorase and cytochrome P450 reductases, in particular, the putidaredoxin reductase of the cytochrome $P450_{cam}$ enzyme system from *Pseudomonas putida*, the flavin (FAD/FMN) domain of the $P450_{BM-3}$ enzyme from *Bacillus megaterium*, spinach ferrodoxin reductase, rubredoxin reductase, adrenodoxin reductase, nitrate reductase, cytochrome $b_5$ reductase, corn nitrate reductase, terpredoxin reductase and yeast, rat, rabbit and human NADPH cytochrome P450 reductases. Where a nitrate reductase is employed preferably corn nitrate reductase is used. Preferred reductases for use in the present invention include diaphorase and putidaredoxin reductases.

The reductase may be a recombinant protein or a naturally occurring protein, which has been purified or isolated. The reductase may have been mutated to improve its performance such as to optimise the speed at which it carries out the electron transfer or its substrate specificity.

The reductase is typically used in an amount of from 1 to 20%, from 2 to 20%, preferably from 3 to 15%, from 5 to 15% by weight relative to the weight of the cholesterol dehydrogenase enzyme.

In a preferred embodiment of the invention, the general scheme of the electrochemical assay is as follows:

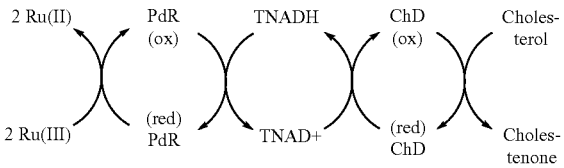

Where:
 PdR—is putidaredoxin reductase
 ChD—is cholesterol dehydrogenase.
One or more additional components may also be provided in the first series of reagents, for example excipients and/or buffers and/or stabilisers. Excipients are preferably provided in order to stabilize the reagents and optionally, where a dried reagent mixture is used, to provide porosity in the dried mixture. Examples of suitable excipients include sugars such as mannitol, inositol and lactose, glycine and PEG. Glycine is preferred. Buffers may also be included to provide the required pH for optimal enzyme activity, which is typically about pH 9. For example, a Tris buffer (pH9) may be used. Stabilisers may be added to enhance, for example, enzyme stability. Examples of suitable stabilisers are amino acids, e.g. glycine, ectoine and myoinositol.

In a preferred embodiment, the first series of reagents comprises a bile acid derivative or a salt thereof, cholesterol esterase or a lipase; cholesterol dehydrogenase; NAD$^+$ or an analogue thereof; a reductase; and a redox agent. In a more preferred embodiment, the reagent mixture comprises CHAPS, deoxy BIGCHAP, cholesterol esterase, cholesterol dehydrogenase, TNAD$^+$, putidaredoxin reductase and Ru(NH$_3$)$_6^{3+}$.

Typically, the total cholesterol test involves contacting the sample with all of the required reagents in a single step. Therefore, a reagent mixture is provided which contains all of the first series of reagents and which can easily be contacted with the sample in order to carry out the assay.

Triglyceride Test

The triglyceride test involves reacting the sample with a second series of reagents comprising a surfactant, a lipase, glycerol dehydrogenase, a coenzyme and a redox agent. A reductase is also preferably used. Typically, the first and second series of reagents are contacted with the sample in separate electrochemical cells. The mixture of sample and reagents is contacted with a working electrode of an electrochemical cell so that redox reactions occurring can be detected. A potential is applied across the cell and the resulting electrochemical response, typically the current, is measured.

Similarly to cholesterol, triglycerides are bound to lipoproteins in their natural form. Surfactants are therefore also used in the triglyceride test in order to break down the lipoproteins and access the triglycerides. Bile acid derivatives and their salts have been found to be effective surfactants for this purpose. Examples of suitable bile acid derivatives include cholic acid, taurocholic acid, glycocholic acid, lithocholic acid, deoxycholic acid, glucodeoxycholic acid, CHAPS (3-[(3-cholamidopropyl)-dimethylammonio]propane), CHAPSO, BIGCHAP and deoxy BIGCHAP. CHAPS is preferred. Combinations of two or more bile acid derivatives or their salts may also be used. The total amount of surfactant used is typically from 5 to 200%, from 5 to 40%, preferably from 15 to 30% by weight relative to the weight of the glycerol dehydrogenase enzyme.

The liberated triglyceride is reacted with a triglyceride hydrolysing reagent to yield one molecule of glycerol per triglyceride molecule. The glycerol is then quantitatively detected using glycerol dehydrogenase. The triglyceride hydrolysing reagent may be any reagent capable of causing the breakdown of triglyceride to glycerol, but which does not interfere with the action of glycerol dehydrogenase. Suitable materials are enzymes such as lipases. Suitable lipases are commercially available, e.g. from Toyobo. For example lipoprotein lipase from *pseudomonas* or *chromobacterium* can be used. The triglyceride hydrolysing reagent is typically used in an amount of from 100 to 300%, from 100 to 250%, preferably from 200 to 250% by weight relative to the weight of the glycerol dehydrogenase enzyme.

The glycerol produced is reacted with glycerol dehydrogenase to provide a reduced form of the glycerol dehydrogenase in accordance with the assay below.

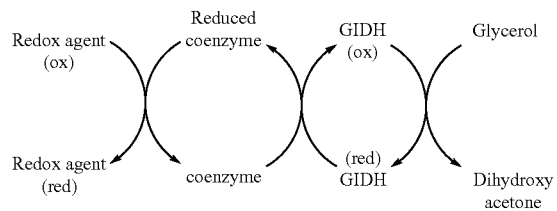

where GlDH is glycerol dehydrogenase. The amount of reduced redox agent produced by the assay is detected electrochemically, thus providing an indication of the total triglyceride content of the sample. Additional reagents may also be included in this assay if appropriate.

Any commercially available form of glycerol dehydrogenase may be employed. For instance, glycerol dehydrogenase can be obtained from Toyobo. Such commercially obtained enzymes may additionally contain stabilisers. Glycerol dehydrogenase may be used in an amount of from 0.1 to 40 mg per 100 µl of sample, from 0.1 to 20 mg per 100 µl, preferably from 0.5 to 20 mg per 100 µl, from 0.5 to 10 mg per 100 µl. The glycerol dehydrogenase and any enzyme employed as the triglyceride hydrolysing reagent may be chemically modified.

The materials used as the coenzyme, redox agent and reductase are typically the same as those set out above with reference to the total cholesterol test, and similar amounts relative to the amount of dehydrogenase enzyme are employed. Thus, the coenzyme is typically used in an amount of from 0.5 to 40% by weight or from 5 to 40% by weight relative to the weight of the glycerol dehydrogenase enzyme. The redox agent is typically used in an amount of from 1 to 70%, from 5 to 60%, preferably from 20 to 60%, from 30 to 60%, preferably from 40 to 60% by weight relative to the weight of the glycerol dehydrogenase enzyme. The reductase is typically used in an amount of from 1 to 20%, from 2 to 20%, preferably from 3 to 15%, from 5 to 15% by weight relative to the weight of the glycerol dehydrogenase enzyme. Stabilisers, excipients and/or buffers of the type described above may also be used. A preferred buffer system for the triglyceride test includes HEPBS buffer (pH9) with potassium hydroxide and ammonium chloride.

The triglyceride assay is preferably as follows:

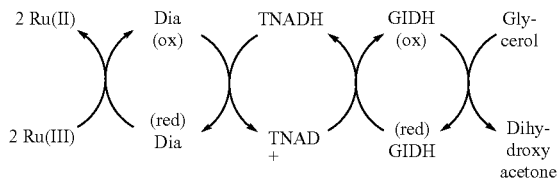

Where
Dia—is diaphorase
GlDH—is glycerol dehydrogenase.

In a preferred embodiment, the second series of reagents comprises a bile acid derivative or a salt thereof; a lipase; glycerol dehydrogenase; NAD$^+$ or an analogue thereof; a reductase; and a redox agent. In a more preferred embodiment, the reagent mixture comprises CHAPS, a lipase, glycerol dehydrogenase, TNAD$^+$, diaphorase and Ru(NH$_3$)$_6^{3+}$.

Typically, the triglyceride test involves contacting the sample with all of the required reagents in a single step. Therefore, a reagent mixture is provided which contains all of the second series of reagents and which can easily be contacted with the sample in order to carry out the assay.

HDL Cholesterol Test

The HDL cholesterol test uses a third series of reagents, which is typically similar to the first series of reagents (for the total cholesterol test), with the exception that reagents providing selectivity for HDL cholesterol over LDL cholesterol are employed.

For example, selectivity may be provided by reacting the sample with a complexing reagent capable of forming a complex with non-HDL lipoproteins, typically LDL and VLDL (very low density lipoproteins). The complexing reagent may also form a complex with chylomicrons (CM). Once in complexed form, the LDL, VLDL and CM are unavailable for reaction with enzymes and therefore do not interfere with the assay described above. In this way, the assay is selective for HDL-cholesterol.

The complexing reagent may form a complex, for example a 1:1 complex, with the LDL, VLDL or CM, or it may form larger aggregates, for example precipitates which may be insoluble in the sample. Such insoluble precipitates do not interfere with the electrochemical detection step. Examples of complexing reagents include polyanions, combinations of polyanions with divalent metal salts, and antibodies capable of binding to apoB containing lipoproteins. The polyanions may be selected from phosphotungstic acid and salts thereof, dextran sulphuric acid and salts thereof, polyethylene glycol and heparin and salts thereof, and are typically present in the reagent mixture in an amount of up to 200 mM, e.g. from 10 to 200 mM, for example from 30 to 150 mM, preferably from 50 to 100 mM. Phosphotungstic acid and its salts are preferred polyanions. The divalent metal salts include the salts of Group IIA metals, e.g. Mg and Ca, and Mn, and are typically present in the reagent mixture in an amount of from 10 to 400 mM, for example from 30 to 300 mM, preferably from 50 to 250 mM, or from 10 to 200 mM, from 30 to 150 mM or from 50 to 100 mM. Mg is a preferred metal. The anion is typically a halide such as chloride, or a sulfate. $MgCl_2$ and $MgSO_4$ are preferred divalent metal salts.

Typically, the HDL cholesterol test involves contacting the sample with all of the required reagents in a single step. Therefore, a reagent mixture is provided which contains all of the third series of reagents and which can easily be contacted with the sample in order to carry out the assay. Typically, the first, second and third series of reagents are contracted with the sample in separate electrochemical cells.

LDL Cholesterol Measurement

Once the above three tests have been completed providing measurements for the total cholesterol, triglyceride and HDL cholesterol content of the sample, the LDL cholesterol content can also be calculated using the Friedwald equation:

$$[LDL] = [\text{Total cholesterol}] - [HDL] - \frac{[\text{Triglyceride}]}{2.17}$$

wherein the concentrations are measured in mM.

In the preferred embodiments of the invention in which all three tests (total cholesterol, triglyceride and HDL cholesterol) are carried out, the tests may be carried out either sequentially or simultaneously. Simultaneously is preferred. Typically, a sample such as a drop of blood is contacted with all three series of reagents at substantially the same time, so that the three electrochemical tests can be carried out at the same time. This has the advantage that the full set of results, including HDL, LDL and total cholesterol measurements, can be provided very rapidly.

Measurements in accordance with the present invention can be carried out on any suitable sample containing cholesterol. Measurements are typically carried out on whole blood or blood components, for example serum or plasma. Preferred samples for use in the method of the present invention are serum and plasma. Where an electrochemical measurement is carried out on whole blood, the measurement obtained may depend on the hematocrit. The measurement should therefore ideally be adjusted to at least partially account for this factor. Alternatively, the red blood cells can be removed by filtering the sample prior to carrying out the assay.

The method of the invention may additionally comprise a step of correcting the obtained measurements for interferents. This step typically involves reacting the sample with a control series of reagents comprising a surfactant, coenzyme, redox agent and optionally a reductase as well as buffers, stabilisers and excipients as desired. Typically, the reagents of the control series are the same reagents, or very similar reagents, to the first, second and third series of reagents, with the exception that one of the components in the enzyme cascade is missing. For example, the enzymes reactive with the triglyceride and cholesterol may not be present. Reaction of the sample with the control reagents, and subsequent measurement of any electrochemical response, enables the skilled person to determine the response due to interfering substances in the sample. The response due to interferents can subsequently be subtracted from the measurements of the total cholesterol, triglyceride and HDL cholesterol tests to give more accurate results wherein the effects of interferents are reduced or eliminated. Further, should the sample tested contain any significant quantities of interfering substances which will cause the test to fail, this can be identified using the control reaction.

Kit for Carrying Out Cholesterol Test

The kit of the present invention comprises a device having one or more electrochemical cells, each cell having a working electrode, a reference or pseudo reference electrode and optionally a separate counter electrode. A series of reagents is associated with one or more of the cells in order that the cell(s) provide the desired electrochemical test. By the reagents being associated with the electrochemical cell, we mean that the reagents are positioned in such a way that once the sample contacts the reagents, the mixture of reagents and sample will contact the working electrode of the electrochemical cell. The kit also comprises a power supply for applying a potential across each cell and a measuring instrument for measuring the resulting electrochemical response of each cell.

The device of the invention typically has at least one electrochemical cell which is associated with the first series of reagents described above. Thus, the kit typically provides at least a measurement of the total cholesterol content of the sample. Alternatively or preferably additionally, the device comprises a second electrochemical cell associated with the second series of reagents described above so that a measurement of the triglyceride content is provided. A third electrochemical cell associated with the third series of reagents described above is preferably present, so that the kit provides a measurement of the total cholesterol, triglyceride and HDL cholesterol contents of the sample. A further preferred embodiment also comprises calculating means, typically a computer program, for determining the LDL cholesterol content of the sample using the Friedwald equation set out above.

Typically, each series of reagents is provided in the device in the form of a single reagent mixture (i.e. one reagent mixture is provided for each series of reagents). The reagent mixture(s) may be present in either liquid or solid form, but are preferably in solid form. Typically, the reagent mixture(s) are inserted into or placed onto the device whilst suspended/dissolved in a suitable liquid (e.g. water) and then dried in position. This step of drying the material into/onto the device helps to keep the material in the desired position, and helps to prevent reagent from migrating from one electrochemical cell of the device to another. Drying may be carried out, for example, by air-drying, vacuum drying, freeze drying or oven drying (heating). The reagent mixture is typically located in the vicinity of the electrodes, such that when the sample contacts the reagent mixture, contact with the electrodes also occurs.

In one embodiment of the invention, the or each electrochemical cell is in the form of a receptacle. The receptacle may be in any shape as long as it is capable of containing a liquid which is placed into it. For example, the receptacle may be cylindrical. Generally, a receptacle will contain a base and a wall or walls which surround the base. In this embodiment, the reagent mixture(s) are typically contained within the receptacle(s) which has the added benefit of ensuring that each of the possible reagent mixtures are separate from one another. Each test can therefore easily be carried out without interference from the other reagent mixtures, even when the electrochemical cells are located very close to one another. Preferably, the electrochemical cells containing reagent mixtures are located within an area of no more than $2 cm^2$, e.g. 1.5 $cm^2$ or 1 $cm^2$, on the device.

Alternatively, the or each cell may be in the form of a partial receptacle. In this embodiment, the cell is designed such that when placed against a separate substrate, the partial receptacle together with the substrate forms a receptacle. In this embodiment, the partial receptacle comprises a wall or walls which connect a first open part with a second open part. The second open part may be placed against a substrate to form a receptacle, such that the substrate forms the true base of the receptacle thus formed. The second open part may, if desired, be covered by a permeable or semi-permeable membrane.

It is preferred that each electrochemical cell has at least one microelectrode. Typically, the working electrode is a microelectrode. For the purposes of this invention, a microelectrode is an electrode having at least one working dimension not exceeding 50 μm. The microelectrodes of the invention may have a dimension which is macro in size, i.e. which is greater than 50 μm.

The 'working dimension' of the electrode is one which is in contact with the test solution during operation. Further, the working dimension is one which causes the electrode to have an electrochemical response which at least in part corresponds to the typical response of a true microelectrode. Without wishing to be bound by any particular theory, an electrode can be considered to have an electrochemical response which is the sum of its 'micro' characteristic response (radial diffusion to the electrode) and its 'macro' characteristic response (semi-infinite diffusion to the electrode). In context of this invention, when determining the electrochemical response 5 seconds after application of a potential using a solution having a 4 cp viscosity, a 'microelectrode' will typically have a response of which at least 50%, preferably at least 60%, more preferably at least 70%, is determined by the 'micro' behavior of the electrode.

An electrochemical cell may be either a two-electrode or a three-electrode system. A two-electrode system comprises a working electrode and a pseudo reference electrode. A three-electrode system comprises a working electrode, a reference electrode and a separate counter electrode. As used herein, a reference or pseudo reference electrode is an electrode that is capable of providing a reference potential. A pseudo reference electrode also acts as the counter electrode and is able to pass a current without substantially perturbing the reference potential.

An electrochemical cell according to one embodiment of the invention is depicted in FIG. 1. In this embodiment, the working electrode 5 is a microelectrode. The cell is in the form of a receptacle or a container having a base 1 and a wall or walls 2. Typically, the receptacle will have a depth (i.e. from top to base) of from 25 to 1000 μm. In one embodiment, the depth of the receptacle is from 50 to 500 μm, for example from 75 to 250 μm, from 100 to 250 μm. In an alternative embodiment, the depth of the receptacle is from 50 to 1000 μm, preferably from 200 to 800 μm, for example from 300 to 600 μm. The length and width (i.e. from wall to wall), or in the case of a cylindrical receptacle the diameter, of the receptacle is typically from 0.1 to 5 mm, for example 0.5 to 1.5 mm, such as 1 mm.

The open end of the receptacle 3 may be partially covered by an impermeable material or covered by a semi-permeable or permeable material, such as a semi-permeable or permeable membrane. Preferably, the open end of the receptacle is substantially covered with a semi-permeable or permeable membrane 4. The membrane 4 serves, inter alia, to prevent dust or other contaminants from entering the receptacle.

The membrane 4 is made of a material through which the sample to be tested can pass. For example, if the sample is plasma, the membrane should be permeable to plasma. The membrane also preferably has a low protein binding capacity. Suitable materials for use as the membrane include polyester, cellulose nitrate, polycarbonate, polysulfone, microporous polyethersulfone films, PET, cotton and nylon woven fabrics, coated glass fibres and polyacrylonitrile fabrics. These fabrics may optionally undergo a hydrophilic or hydrophobic treatment prior to use. Other surface characteristics of the membrane may also be altered if desired. For example, treatments to modify the membrane's contact angle in water may be used in order to facilitate flow of the desired sample through the membrane. The membrane may comprise one, two or more layers of material, each of which may be the same or different. For example, conventional double layer membranes comprising two layers of different membrane materials may be used.

The membrane may also be used to filter out some components which are not desired to enter the cell. For example, some blood products such as red blood cells, erythrocytes and/or lymphocytes may be separated out in this manner such that these particles do not enter the cell. Suitable filtration membranes, including blood filtration membranes, are known in the art. Examples of blood filtration membranes are Presence 200 and PALL BTS SP300 of Pall filtration, Whatman VF2, Whatman Cyclopore, Spectral NX and Spectral X. Fibreglass filters, for example Whatman VF2, can separate plasma from whole blood and are suitable for use where a whole blood specimen is supplied to the device and the sample to be tested is plasma.

For the purposes of this embodiment of the invention, the sample is the material which (when mixed with the reagent mixture) contacts the working electrode. In one embodiment, a specimen comprising the sample is supplied to the device of the invention and the specimen is filtered through the membrane prior to contacting the working electrode. For example, the specimen may be whole blood and the method may comprise the step of removing red blood cells from the specimen (e.g. using a blood filtration membrane) such that, for example, only plasma or serum contacts the working electrode. In this case, the sample is plasma or serum.

The electrochemical cell of this embodiment of the invention contains a working electrode 5 which is situated in a wall of the receptacle. The working electrode is, for example, in the form of a continuous band around the wall(s) of the receptacle. The thickness of the working electrode is typically from 0.01 to 50 μm, from 0.01 to 25 μm, preferably from 0.05 to 15 μm, for example 0.1 to 20 μm. Thicker working electrodes are also envisaged, for example electrodes having a thickness of from 0.1 to 50 μm, preferably from 5 to 20 μm. The thickness of the working electrode is its dimension in a vertical direction when the receptacle is placed on its base. The working electrode is preferably formed from carbon, palladium, gold or platinum, for example in the form of a conductive ink. The conductive ink may be a modified ink containing additional materials, for example platinum and/or graphite. Two or more layers may be used to form the working electrode, the layers being formed of the same or different materials.

The cell also contains a pseudo reference electrode which may be present, for example, in the base of the receptacle, in a wall or walls of the receptacle or in an area of the device surrounding or close to the receptacle. The pseudo reference electrode is typically made from Ag/AgCl, although other materials may also be used. Suitable materials for use as the pseudo reference electrode will be known to the skilled person in the art. In this embodiment, the cell is a two-electrode system in which the pseudo reference electrode acts as both counter and reference electrodes. Alternative embodiments in which the cell comprises a reference electrode and a separate counter electrode can also be envisaged.

The pseudo reference (or reference) electrode typically has a surface area which is of a similar size to or smaller than, or which is larger than, for example substantially larger than, that of the working electrode 5. Typically, the ratio of the surface area of the pseudo reference (or reference) electrode to that of the working electrode is at least 1:1, for example at least 2:1 or at least 3:1. A preferred ratio is at least 4:1. The pseudo reference (or reference) electrode may, for example, be a macroelectrode. Preferred pseudo reference (or reference) electrodes have a dimension of 0.01 mm or greater, for example 0.1 mm or greater. This may be, for example, a diameter of 0.1 mm or greater. Typical areas of the pseudo reference (or reference) electrode are from 0.001 $mm^2$ to 100 $mm^2$, preferably from 0.01 $mm^2$ to 60 $mm^2$, for example from 0.1 $mm^2$ to 50 $mm^2$. The minimum distance between the working electrode and the pseudo reference (or reference) electrode is, for example from 10 to 1000 μm.

In order that the cell can operate, the electrodes must each be separated by an insulating material 6. The insulating material is typically a polymer, for example, an acrylate, polyurethane, PET, polyolefin, polyester or any other stable insulating material. Polycarbonate and other plastics and ceramics are also suitable insulating materials. The insulating layer may be formed by solvent evaporation from a polymer solution. Liquids which harden after application may also be used, for example varnishes. Alternatively, cross-linkable polymer solutions may be used which are, for example, cross-linked by exposure to heat or UV or by mixing together the active parts of a two-component cross-linkable system. Dielectric inks may also be used to form insulating layers where appropriate. In an alternative embodiment, an insulating layer is laminated, for example thermally laminated, to the device.

The electrodes of the electrochemical cell may be connected to any required measuring instruments by any suitable means. Typically, the electrodes will be connected to electrically conducting tracks which are, or can be, themselves connected to the required measuring instruments.

The required reagents are typically contained within the receptacle, as depicted at 7 in FIG. 1. Typically, the reagents, in the form of a single reagent mixture, are inserted into the receptacle in liquid form and subsequently dried to help immobilise the composition. Preferably the reagent mixture is freeze dried. On introduction of the sample into the receptacle, the dried material is re-suspended forming a liquid comprising the reagents and the sample, the liquid being in contact with the working electrode which is located in the wall of the receptacle. The liquid is also typically in contact with the reference and counter electrodes (3-electrode system) or with the pseudo reference electrode (2-electrode system). Thus, on application of a voltage across the cell, electrochemical reaction may occur and a measurable response (e.g. a current) be produced. Typically, where a membrane is present over the receptacle, a wet-up time is provided before a voltage is applied, to allow the dried material to re-suspend. Clearly, the wet-up time will depend on the specific device used. The precise wet-up time is not therefore an important feature of the invention. Simply as an example, a wet-up time of 20 seconds, or from 1 second to 5 minutes, may be mentioned.

The receptacle may, for example, contain one or more small air-holes in its base or its wall or walls (not depicted in FIG. 1). These holes allow air to escape from the receptacle when sample enters the receptacle. If such air-holes are not present, the sample may not enter the receptacle when it flows over the open end, or it may enter the receptacle only with difficulty. The air holes typically have capillary dimensions, for example, they may have an approximate diameter of 1-600 μm, for example from 100 to 500 μm. The air holes should be sufficiently small that the sample is substantially prevented from leaving the receptacle through the air holes due to surface tension. As an example, from 1 to 4 air holes may be present.

The cell may optionally comprise a separate counter electrode in addition to the working and reference electrodes. Suitable materials for producing the counter electrode will be known to the skilled person in the art. Ag/AgCl is an example of a suitable material.

Figure 2:
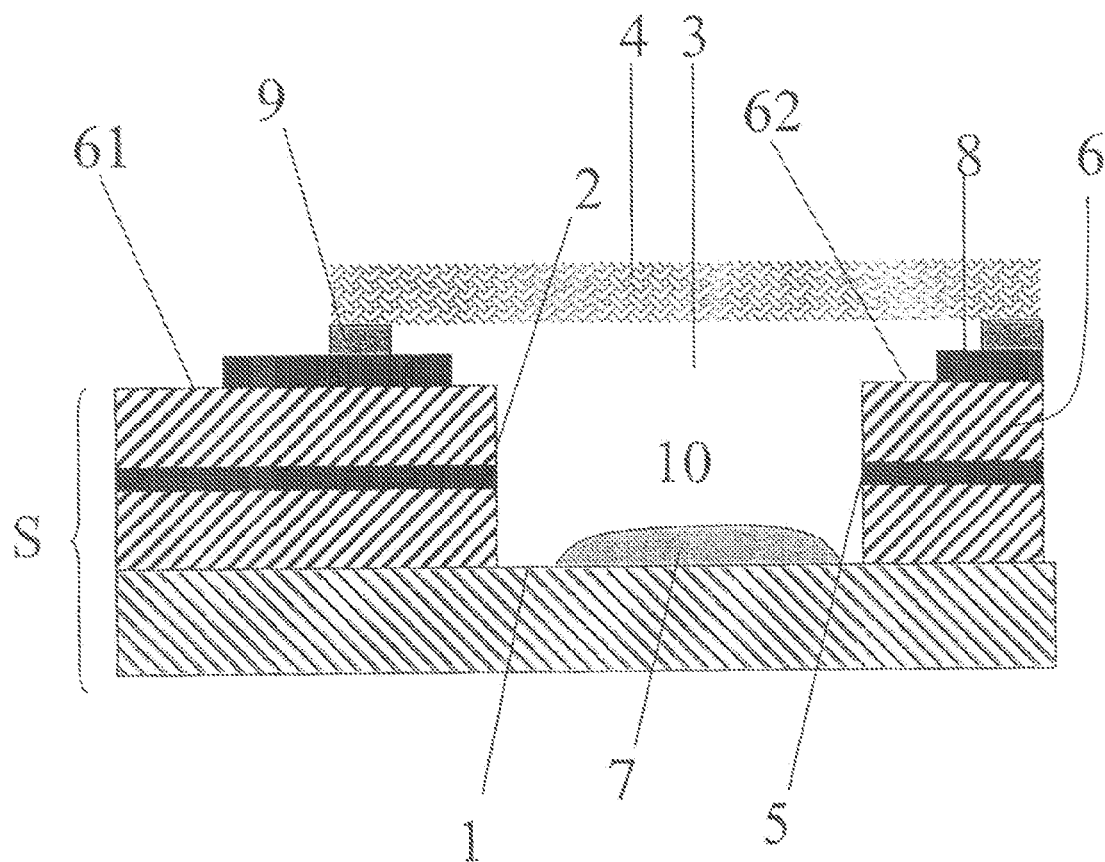
FIG. 2 depicts an alternative electrochemical cell according to the invention.

An alternative electrochemical cell is depicted in FIG. 2. This embodiment is the same as that depicted in FIG. 1 and described above, except as set out below. In this embodiment, the device comprises a strip S. The strip S may have any shape and size, but typically has a first surface 61, 62 which is substantially flat. The strip comprises a receptacle 10 bounded by base 1 and wall or walls 2. The device further comprises an electrochemical cell having a working electrode 5 in the wall(s) of the receptacle. The working electrode is typically a microelectrode.

The device of this embodiment comprises a pseudo reference electrode acting as reference electrode and also as counter electrode. Alternatively, separate counter and reference electrodes may be used. The pseudo reference (or reference) electrode comprises a pseudo reference (or reference) electrode layer 8 present on the first surface of the strip 61, 62. The first surface of the strip is an external surface, i.e. it is a surface exposed to the outside of the device rather than a surface exposed to the interior of the receptacle. Typically, the pseudo reference (or reference) electrode layer substantially surrounds the receptacle or partial receptacle 10. As depicted in FIG. 2, it is preferred that the pseudo reference (or reference) electrode layer is not in contact with the perimeter of the first open part 3. Typically, the pseudo reference (or reference) electrode layer is at a distance of at least 0.1 mm, preferably at least 0.2 mm from the perimeter of the first open part. At least a part of the pseudo reference (or reference) electrode is, however, typically no more than 5 mm, for example no more than 2 mm, for example no more than 1 mm or 0.5 mm, preferably no more than 0.4 mm from the perimeter of the first open part. In one embodiment, the pseudo reference (or reference) electrode substantially surrounds the receptacle or partial receptacle at a distance of from 0.01 to 1.0 mm, for example from 0.1 to 0.5 mm, or 0.2 to 0.4 mm from the perimeter of the first open part. Alternatively, this distance may be from 0.01 to 0.3 mm or from 0.4 to 0.7 mm or 0.4 to 0.8 mm.

The thickness of the pseudo reference (or reference) electrode is typically similar to or greater than the thickness of the working electrode. Suitable minimum thicknesses are 0.1 µm, for example 0.5, 1, 5 or 10 µm. Suitable maximum thicknesses are 50 µm, for example 20 or 15 µm.

The pseudo reference (or reference) electrode 8 typically has a surface area which is of a similar size to (or smaller than), or which is larger than, for example substantially larger than, that of the working electrode 5. Typically, the ratio of the surface area of the pseudo reference (or reference) electrode to that of the working electrode is at least 1:1, for example at least 2:1 or at least 3:1 preferably at least 4:1. The pseudo reference (or reference) electrode may, for example, be a macroelectrode. Where the ratio of the surface area of the pseudo reference (or reference) electrode to that of the working electrode is greater than 1:1, this helps to ensure that the electrochemical reaction occurring at the pseudo reference (or reference) electrode is not current-limiting. The actual area of the pseudo reference (or reference) electrode is, for example, from 0.001 $mm^2$ to 100 $mm^2$ or from 0.01 $mm^2$ to 60 $mm^2$, for example from 0.1 $mm^2$ to 50 $mm^2$.

A membrane 4 may be attached to the device by any suitable attachment means 9, for example using a double-sided adhesive tape. Typically, the attachment means attaches the membrane to the first surface of the strip or to the pseudo reference (or reference) electrode layer. In a preferred embodiment as depicted in FIG. 2, the membrane is attached to the pseudo reference (or reference) electrode layer 8 at a location which is remote from the perimeter of the receptacle itself. Further, the attachment means is at a greater distance from the first open part of the receptacle 3 than the pseudo reference (or reference) electrode layer, such that at least a part of the surface of the pseudo reference (or reference) electrode layer close to or surrounding the receptacle is exposed to a sample which has passed through the membrane. Preferably, the attachment means is at least 0.2 mm, for example at least 0.3 mm or at least 0.4 mm, from the perimeter of the receptacle.

In the embodiment depicted in FIG. 2, a reaction volume is defined by the receptacle base 1 and walls 2, part of the surface of the strip 61, 62, the pseudo reference (or reference) electrode layer 8, the attachment means 9 and the membrane 4. This reaction volume can be varied by changing the volume of the receptacle, the position and thickness of the pseudo reference (or reference) electrode layer and the position and thickness of the attachment means 9. Preferred reaction volumes are at least 0.05 µl, for example at least 0.1 µl or 0.2 µl. It is further preferred that the reaction volume is no more than 25 µl, preferably no more than 5 µl, for example no more than 2 µl or no more than 1 µl. A typical reaction volume is approximately 0.8 µl.

The devices depicted in FIGS. 1 and 2 comprise receptacles having a base 1. In an alternative embodiment of the invention the base 1 may be absent such that a second open part is located at 1. In this embodiment, the device comprises a partial receptacle. Optionally, a permeable or semi-permeable membrane is placed over the second open part, for example a hydrophobic breathable membrane, e.g. Pall Versapor by Pall Filtration.

Further details regarding electrochemical cells which can be used in the devices of the present invention can be found in International Application No. PCT/GB05/002557. The content of this application is incorporated herein by reference in its entirety.

Figure 3:
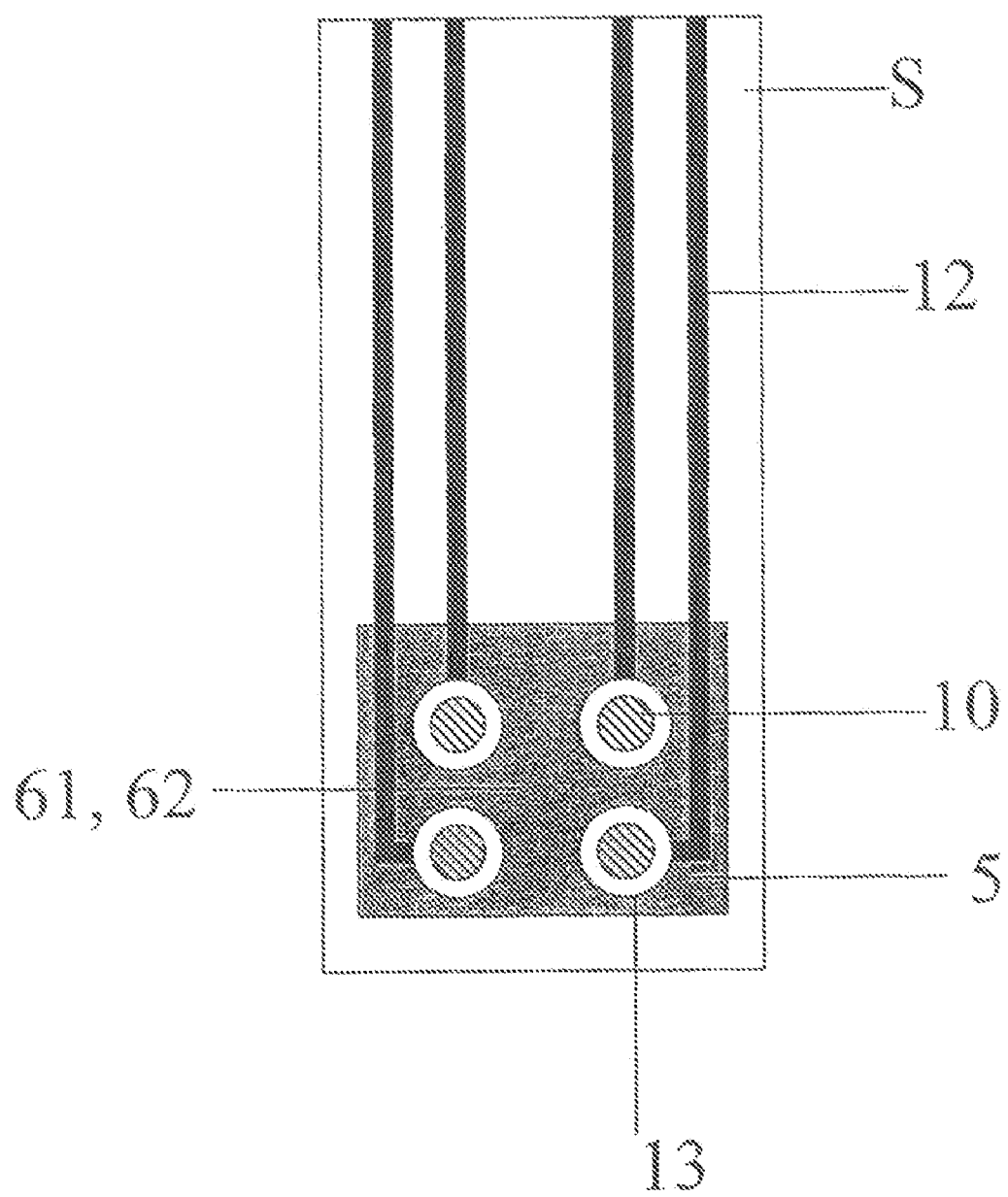
FIG. 3 depicts a device according to the invention for carrying out multiple electrochemical tests.

The devices of the invention preferably comprise two or more (e.g. three or four) electrochemical cells. A device of this type, having four electrochemical cells 10 on a strip S, is depicted in FIG. 3. Each cell comprises a working electrode and may additionally comprise a counter electrode. Preferably, and as depicted in FIG. 3, a single layer of pseudo reference electrode material 5 is provided on the surface of the strip 61,62, surrounding each receptacle and leaving a blank area 13 between the perimeter of the receptacle and the edge of the pseudo reference electrode layer. The electrodes are connected to the required instruments via conductive tracks 12.

This embodiment of the invention allows a number of measurements to be taken simultaneously. In a preferred aspect of this embodiment, three of the cells contain reagent mixtures corresponding to the first, second and third reagent mixtures described above. A fourth cell is typically a control cell. The control cell does not contain any enzyme reagent which is reactive with triglyceride or cholesterol, but typically contains the control series of reagents described above. The presence of the control cell therefore enables the user to correct the obtained results to reduce or eliminate errors due to interferents.

The kit of the invention may comprise a strip S containing the electrochemical cell(s) (e.g. that depicted in FIG. 2 and described above) and an electronics unit, e.g. a hand-held portable electronics unit, capable of forming electronic contact with the strip S. The electronics unit may, for example, house the power supply for providing a potential to the electrodes, as well as a measuring instrument for detecting an electrochemical response and any other measuring instruments required. The electronics unit may also include a calculator for determining the LDL cholesterol content. One or more of these systems may be operated by a computer program.

The devices of the invention can be produced by forming a laminate structure comprising a layer of working electrode material (e.g. a layer of graphite) between two layers of insulating material. A hole (or several holes where several electrochemical cells are required) is then punched (or drilled or cut) through this laminate, thus forming the wall(s) of the receptacle. A base, optionally comprising a counter electrode, is then added. The counter electrode may alternatively be provided by printing a layer of a suitable material onto the insulating material surrounding, or close to, the open part of the receptacle. Where an air hole is desired in the base or wall(s) of the receptacle, this can be formed by any suitable technique, for example by drilling or punching a hole or by use of an air permeable membrane as the base. Full details regarding the process for producing cells as depicted in FIGS. 1 and 2 can be obtained from International Application No. PCT/GB05/002557, which is referenced above.

The device of the present invention is operated by providing a sample to the device and enabling the sample to contact the reagent mixture or mixtures. The device of the embodiment depicted in FIG. 3 desirably contains all four electrochemical cells within a small area, e.g. within about 1 cm², so that all four electrochemical cells are wetted by providing a small amount of sample, e.g. a drop of blood. Typically a wet-up time, merely as an example, of approximately 20 seconds, is provided to enable the reagent mixtures to be dissolved/suspended in the sample and to allow reaction to occur. The sample/reagent mixtures should be in electronic contact with the working electrode in each cell in order that electrochemical reaction can occur at the electrode.

A potential is then applied across each cell and, typically, the current produced is measured. Typically, the potential is applied after allowing a suitable time period for reaction. In practice, such a time period is chosen such that it is suitable for a commercial device. Thus, although in no way limited, typically, the potential is applied after a period of time of, for example, up to 5 minutes or up to 3 minutes after providing the sample to the device. This period is preferably from 1 second to 180 seconds or 10 seconds to 180 seconds, e.g. up to 90 seconds, for example from 15 seconds to 1 minute, from 15 seconds to 30 seconds or approximately 20 seconds. The use of periods within this preferred range may be particularly important when an HDL cholesterol test is included. The use of short time frames helps to ensure that the measurement detects only cholesterol bound to HDL. Where longer periods are used, some cholesterol bound to non-HDL lipoproteins, e.g. LDL, may also react leading to an inaccurate measurement of the HDL-cholesterol content.

Typically, where Ru(II) is the product to be detected at the working electrode, the potential applied to the cell is from −0.3 to 0.3V, for example from −0.1 to −0.3V or from 0.1 to 0.3V. Where Ru(III) is the product to be detected, the potential applied to the cell may be or −0.4V or lower, for example from −0.4V to −0.6V. Preferred applied potentials are 0.15V and −0.45V. Preferably, the potential applied to the cell is from 0.1 to 0.3V, and a preferred applied potential is 0.15V. (All voltages mentioned herein are quoted against a Ag/AgCl reference electrode). In a preferred embodiment, the potential is stepped first to a positive applied potential, e.g. 0.1 to 0.2V, for a period of between 0.1 to 10 seconds, more preferably 1 to 4 seconds, for example about 1 second, and then stepped to a negative applied potential of −0.4 to −0.6V for an equivalent time period to that used in the first potential step, for example for a further 1 second. The use of the double potential step enables correction for electrode fouling and variation in electrode area to be minimized, as is described in WO 03/097860 (incorporated herein by reference in its entirety). Where a different redox agent is used, the applied potentials can be varied in accordance with the potentials at which the oxidation/reduction peak occurs.

EXAMPLES

Example 1

A device of the type depicted in FIG. 3, having four electrochemical cells as depicted in FIG. 2 wherein the base 1 is formed by a membrane (Pall Versapor) is used. The working electrode is a carbon electrode and the pseudo reference electrode is a Ag/AgCl electrode. The volume of each cell as defined by the walls, base, adhesive and bottom surface of the membrane 4 is approximately 0.8 μl. A reagent mixture is inserted into each cell and freeze dried, prior to attachment of a Whatman VF2 membrane over the device at 4.

The reagent mixtures used are as follows. Batches of reagent mixture are made up in advance using the proportions specified below.

Total Cholesterol Test (0.6 μl Inserted into the Electrochemical Cell)
0.1 M TRIS buffer (pH9)
0.05 M Magnesium sulphate ($MgSO_4$)
5% w/v Sigma CHAPS
5% Soltec Ventures deoxy bigCHAP
5% w/v glycine
1% w/v inositol
1% w/v ectoine
80 mM ruthenium (III) hexamine chloride ($Ru(NH_3)_6Cl_3$)
8.8 mM thio-nicotinamide adenine dinucleotide (TNAD)
4.2 mg/ml putidaredoxin reductase (PdR), (activity 8.6 u/mg)
3.3 mg/ml cholesterol esterase (ChE) (activity 136 u/mg)
66 mg/ml cholesterol dehydrogenase (ChDH) activity 39 u/mg)

Triglyceride Test (0.7 μl Inserted into the Electrochemical Cell)
0.1 M HEPBS buffer (pH9)
0.01 M Ammonium chloride ($NH_4Cl$)
1% w/v Sigma CHAPS
10% w/v glycine
1% w/v ectoine
80 mM ruthenium (III) hexamine chloride ($Ru(NH_3)_6Cl_3$)
17.6 mM thio-nicotinamide adenine dinucleotide (TNAD)
6.5 mg/ml diaphorase (activity 10 u/mg)
45 mg/ml glycerol dehydrogenase (activity 90 u/mg)
100 mg/ml lipase (activity 34 u/mg)

HDL Cholesterol Test (0.3 μl Inserted into the Electrochemical Cell)
0.1 M TRIS (pH8)
2% $MgCl_2$
2% B66
3% glycine
1% Lactitol
lactose 1%
1% hydroxyectoine
20 mM $Ru(NH_3)_6Cl_3$
5 mM TNAD
6 mg/ml PdR
10 mg/ml Genzyme Lipase
ChDH 20 mg/ml Blank (0.6 μl Inserted into the Electrochemical Cell)
0.1M HEPBS (pH9)
0.01M $NH_4Cl$
1% w/v Sigma CHAPS
10% w/v glycine
1% w/v ectoine
80 mM ruthenium (III) hexamine chloride ($Ru(NH_3)_6Cl_3$)
17.6 mM TNAD
6.5 mg/ml diaphorase (activity 10 u/mg)
4.2 mg/ml putidaredoxin reductase (activity 8.6 u/mg)

A number of specimens having unknown cholesterol contents are supplied to the device in a series of experiments. A wet-up period of 20 seconds is allowed to elapse to permit up-take of the reagents in the sample and reaction between the reagents and the sample. A potential of +0.15V is then applied across each cell for 1 second followed by a potential of −0.45V for a further 1 second. The current is measured and the amount of total cholesterol, triglyceride or HDL cholesterol respectively is calculated.

Examples 2 to 13

Analysis Used for Examples 2 to 13

The output from General Purpose Electrochemical System (GPES) software (Eco Chemie) software was analysed using the concentrations of appropriate analyte, for example total cholesterol, triglycerides, dilipidated serum, obtained from a Space analyser. The precision (% CV) of the readings for each sample was calculated on the template using the formula:

$$\% \, CV = \frac{100 \times StDev}{Average}$$

StDev is the standard deviation of the results from a given sample, and average is the mean value.

Total Cholesterol Test

Example 2

Freeze Dried Sensors Prepared with Various Surfactants

Several experiments were performed using the same basic enzyme mix, with a number of different surfactants. The basic enzyme mix dispensing mixture was prepared as followed. Tris buffer containing $MgSO_4$, glycine, myo-inositol, ectoine was used to make solutions containing $Ru(NH_3)_6Cl_3$ and thio-nicotinamide adenine dinucleotide (TNAD), putidaredoxin reductase (PdR), cholesterol esterase (ChE), surfactant which were subsequently used to make a single solution containing cholesterol dehydrogenase (ChDH).

Approximate concentrations in final mix:
0.1 M Tris buffer (pH 9.0)
50 mM $MgSO_4$
5% w/v glycine
1% w/v myo-inositol
1% w/v ectoine
Varying % surfactant (see below)
80 mM $Ru(NH_3)_6Cl_3$ (in the case of 7.5% DBC the Ruthenium concentration was 40 mM)
8.8 mM TNAD
4.2 mg/ml PdR
3.3 mg/ml ChE
100 mg/ml ChDH Concentrations of surfactants tested in final dispensed mixture:
No surfactant
5% CHAPS
5% CHAPSO
5% glucodeoxycholic acid
10% DeoxyBigCHAP(DBC)
7.5% DeoxyBigCHAP(DBC)
9% DeoxyBigCHAP(DBC): 1% CHAPS
7.5% DeoxyBigCHAP(DBC): 2.5% CHAPS
5% DeoxyBigCHAP(DBC): 5% CHAPS
2.5% DeoxyBigCHAP(DBC): 7.5% CHAPS
10% CHAPS Freeze Drying Sensors:

A 0.6 µl aliquot of the above mixtures was dispensed per well by hand. Once dispensed, the solutions in the sensors were freeze dried. Screen printed sensors had laser drilled wells.

Figure 4:
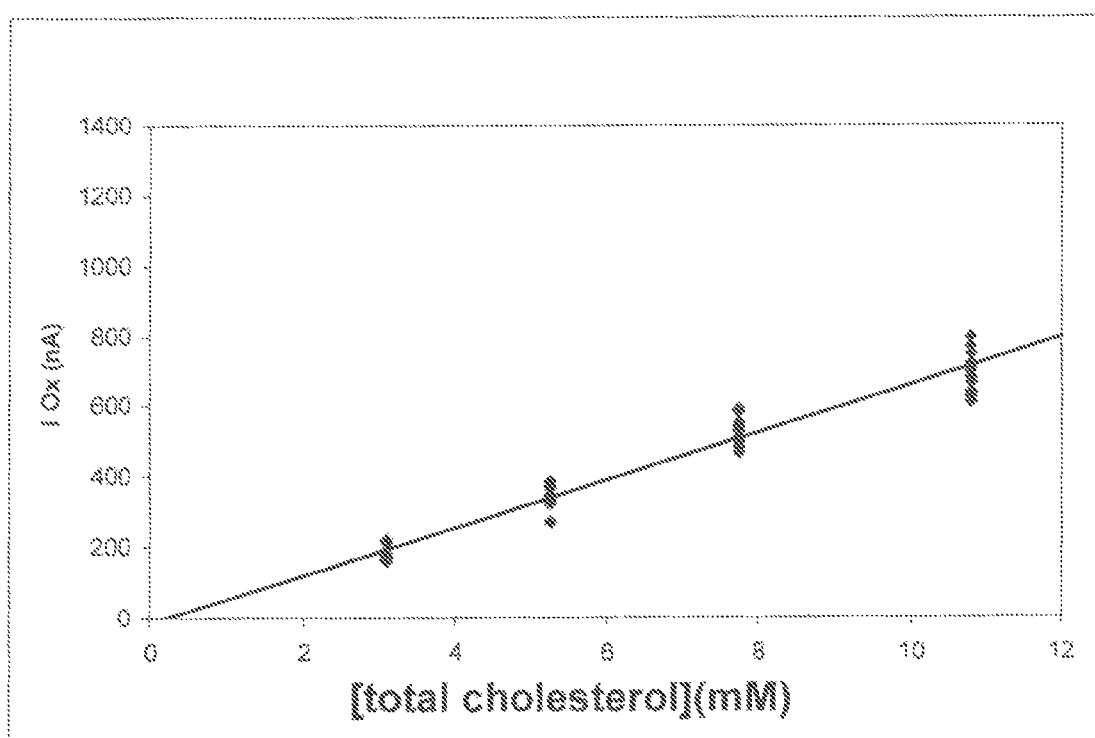
FIG. 4 shows an example of a typical calibration plot of oxidation current versus the total cholesterol concentration for different human plasma samples using 7.5% DeoxyBigCHAP(DBC):2.5% CHAPS as the surfactant in the total cholesterol sensor.

Standard Electrochemical Testing Protocol:

The sensors were prepared with double sided Arcare adhesive (Adhesives Research) and a Petex spreading membrane. An aliquot (5 µl) of sample was applied per sensor. The samples used were anonymised plasma samples. The sensors were tested by chronoamperometry using an Autolab PGSTAT 12 (Eco Chemie) attached to a multiplexer (MX452, Sternhagen Design) controlled by the GPES software. At T=0 seconds the chronoamperometry test was initiated using the multiplexer attached to the Autolab. Repeat oxidations (5) at +0.15V for 1 second were performed. There was a 30 second delay between oxidations which resulted in oxidations at approximately 0, 30, 60, 90 and 120 seconds. Data was analysed for current values at 1 second on the transient. This procedure was then repeated for several different plasma samples with a range of total cholesterol concentrations in order to obtain a calibration plot of current versus analyte concentration. An example of a typical calibration plot of oxidation current versus the total cholesterol concentration for different human plasma samples using 7.5% DeoxyBigCHAP(DBC):2.5% CHAPS as the surfactant in the total cholesterol sensor is shown in FIG. 4. The results are shown in Table 1.

TABLE 1

Electrochemical response of freeze dried total cholesterol sensors prepared with various surfactants.

| Surfactant | Gradient nA/mM |
|---|---|
| 0% | 22.2 |
| 5% CHAPS | 69.3 |
| 5% CHAPSO | 90.5 |
| 5% glucodeoxycholic acid | 72.4 |
| 10% DBC | 50.1 |
| 9% DBC & 1% CHAPS | 60.5 |
| 7.5% DBC & 2.5% CHAPS | 68.0 |
| 5% DBC & 5% CHAPS | 92.6 |
| 2.5% DBC & 7.5% CHAPS | 81.7 |
| 10% CHAPS | 104.0 |
| 7.5% deoxy bigCHAP | 50.6 |

Example 3

Several experiments were performed using the same basic enzyme mix, with variations in the percentage of taurocholic acid (TC). The basic enzyme mix dispensing mixture was prepared as follows. HEPBS buffer containing $MgSO_4$, mannitol was used to make solutions containing $Ru(NH_3)_6Cl_3$ and TNAD, PdR, ChE, surfactant which were subsequently used to make a single solution containing ChDH. Lipase was used instead of cholesterol esterase to break down the lipoproteins.

Approximate concentrations in final mix:
0.1 M HEPBS (pH 9.0)
100 mM $MgSO_4$
2.5% w/v Mannitol
Varying % surfactant (see below)
80 mM $Ru(NH_3)_6Cl_3$
13.3 mM NAD
11.1 mg/ml PdR
20 mg/ml lipase
200 mg/ml ChDH Concentrations of surfactants tested in final dispensed mixture:
1% Taurocholic acid
5% Taurocholic acid
7.5% Taurocholic acid
10% Taurocholic acid
12.5% Taurocholic acid
15% Taurocholic acid A 0.3 µl aliquot of the above mixtures was dispensed per well by hand and freeze dried as described in Example 2. Screen printed sensors had laser drilled wells.

Sensors were tested as detailed in the Standard electrochemical testing protocol given in Example 2. Results are shown in Table 2.

TABLE 2

Electrochemical response of freeze dried total cholesterol sensors prepared with various concentrations of taurocholate (TC).

| Surfactant | Gradient nA/mM |
|---|---|
| 1.0% TC | 108 |
| 5.0% TC | 122 |
| 7.5% TC | 135 |
| 10.0% TC | 118 |
| 12.5% TC | 111 |
| 15.0% TC | 141 |

The results for esterase (Example 2) and lipase (Example 3) are compared in Table 3 below.

TABLE 3

Electrochemical response of freeze dried total cholesterol sensors prepared using either lipase or cholesterol esterase to break down the lipoproteins.

| Enzyme | Gradient nA/mM |
|---|---|
| Esterase (10% CHAPS) | 104 |
| Lipase (10% total cholesterol) | 118 |

Example 4

Alternative Redox Agents (i) $Ru(acac)_2(Py-3-CO_2H)(Py-3-CO_2)$

The enzyme mix dispensing mixture was prepared as follows. Tris buffer containing glycine, $MgSO_4$, myo-inositol, ectoine, CHAPS, deoxybig CHAP was used to make the final solution containing $Ru(acac)_2(Py-3-CO_2H)(Py-3-CO_2)$, TNAD, PdR, ChE and ChDH.

Approximate concentrations in final mix:
0.1M Tris (pH 9.0)
100 mM $MgSO_4$
700 mM glycine
60 mM myo-inositol
70 mM ectoine
82 mM CHAPS
58 mM deoxybigCHAP
50 mM $Ru(acac)_2(Py-3-CO_2H)(Py-3-CO_2)$
9 mM TNAD
4 mg/ml PdR
3.5 mg/ml cholesterol esterase
65 mg/ml ChDH The above mixture (0.3 µl) was dispensed onto each sensor and freeze dried before testing with human plasma samples.

Figure 5:
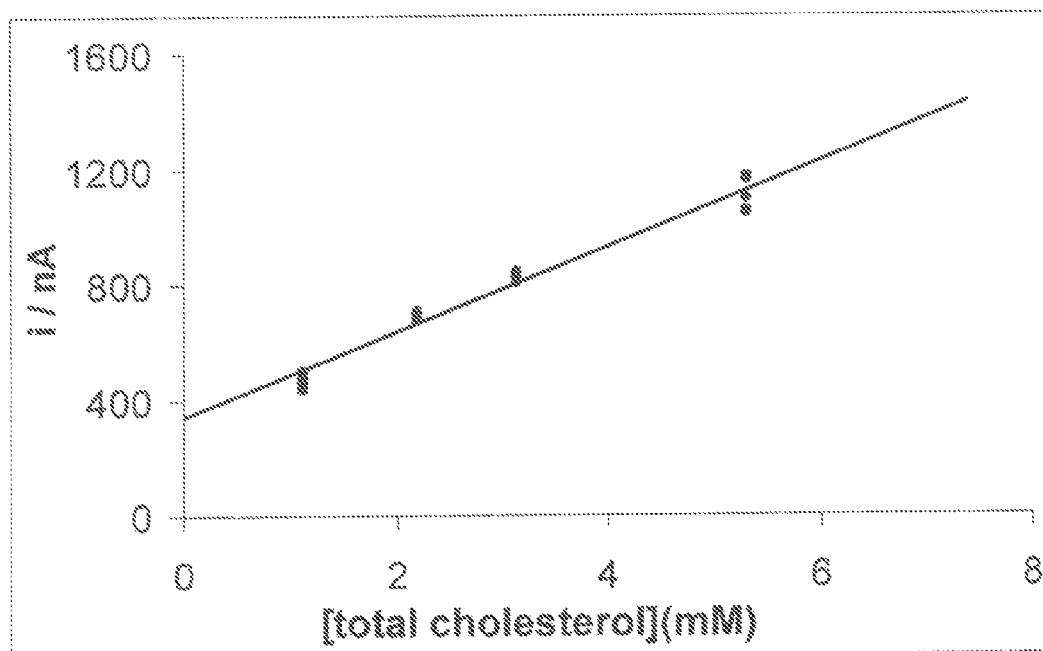
FIG. 5 shows a calibration plot of oxidation current versus the total cholesterol concentration for different human plasma samples using $Ru(acac)_2(Py-3-CO_2H)(Py-3-CO_2)$] and 5% CHAPS in the total cholesterol sensor.

Sensors were tested as detailed in the Standard electrochemical testing protocol given in Example 2. A typical calibration plot is shown in FIG. 5. FIG. 5 shows a calibration plot of oxidation current versus the total cholesterol concentration for different human plasma samples using $Ru(acac)_2(Py-3-CO_2H)(Py-3-CO_2)]$ and 5% CHAPS in the total cholesterol sensor, with a gradient of 148.0 nA/mM. Results are shown in Table 4.

(ii) Potassium Ferricyanide

The enzyme mix dispensing mixture was prepared as follows. Tris buffer containing glycine, myo-inositol, ectotine, CHAPS, deoxybig CHAP was used to make the final solution containing potassium ferricyanide, TNAD, PdR, ChE and ChDH.

Approximate concentrations in final mix:
0.1 M Tris (pH 9.0)
170 mM glycine
14 mM myo-inositol
18 mM ectoine
20 mM CHAPS
38 mM deoxyBigCHAP
75 mM potassium ferricyanide
9 mM TNAD
4 mg/ml PdR
3.3 mg/ml cholesterol esterase
66 mg/ml ChDH The above mixture (0.3 µl) was dispensed onto each sensor and freeze dried before testing with human plasma samples.

Sensors were tested as detailed in the Standard electrochemical testing protocol given in Example 1. Results are show in Table 4.

TABLE 4

Effect of changing the redox agent in the total cholesterol sensor.

| Redox agent | Gradient (nA/mM) |
|---|---|
| $Ru(NH_3)_6$ | 93 |
| Ferricyanide | 229 |
| $Ru(acac)_2(Py-3-CO_2H)(Py-3-CO_2)]$ | 148 |

Example 5

Coenzyme Derivatives (i) Freeze Dried Total Cholesterol Sensors Prepared with TNAD Tris buffer containing $MgSO_4$ and mannitol was used to make solutions containing $Ru(NH_3)_6Cl_3$ and TNAD, PdR, ChE, sodium taurocholate which were subsequently used to make a single solution containing ChDH.

A 0.3 µl aliquot of solution was dispensed per well, and freeze dried.

Arcare adhesive and Petex spreading membrane were applied to the sensors. Sensors were tested with defrosted plasma samples. A delipidated serum sample (Scipac) was also tested. The volume of sample applied to each sensor using a pipette was 5 µl. The sensors were tested by chronoamperometry using an Autolab (PGSTAT 12) and a multiplexer (MX452, Sternhagen Design). At T=0 seconds the chronoamperometry test was initiated using the multiplexer attached to the Autolab. The oxidation current was measured at +0.15V for 1 second, followed by a reduction current measured at −0.45V for 1 second. The data was analysed for current values at 1 second on the transient. Results are show in Table 5.

(ii) Freeze Dried Sensors Prepared with TNADK$^+$

The basic enzyme mix was prepared as follows:
Tris buffer containing MgSO$_4$, Glycine, Myo-inositol, Ectoine, CHAPS, deoxybigCHAP was used to make two solutions containing Ru(NH$_3$)$_6$Cl$_3$, PdR, ChE, ChDH; and TNADK$^+$ which were subsequently combined.

Approximate Concentrations in Final Mix:
0.2 M Tris (pH 9.0)
50 mM MgSO$_4$
5% w/v glycine
1% w/v myo-inositol
1% w/v ectoine
5% w/v Chaps
5% w/v deoxybig CHAP
80 mM Ru(NH$_3$)$_6$Cl$_3$
8.8 mM TNADK$^+$
4.2 mg/ml PdR
3.3 mg/ml ChE
66 mg/ml ChDH Freeze Drying Sensors:

A 0.4 µl aliquot was dispensed per well by hand. Once dispensed the solutions in the sensors were freeze dried. Screen printed sensors had laser drilled wells.

Figure 6:
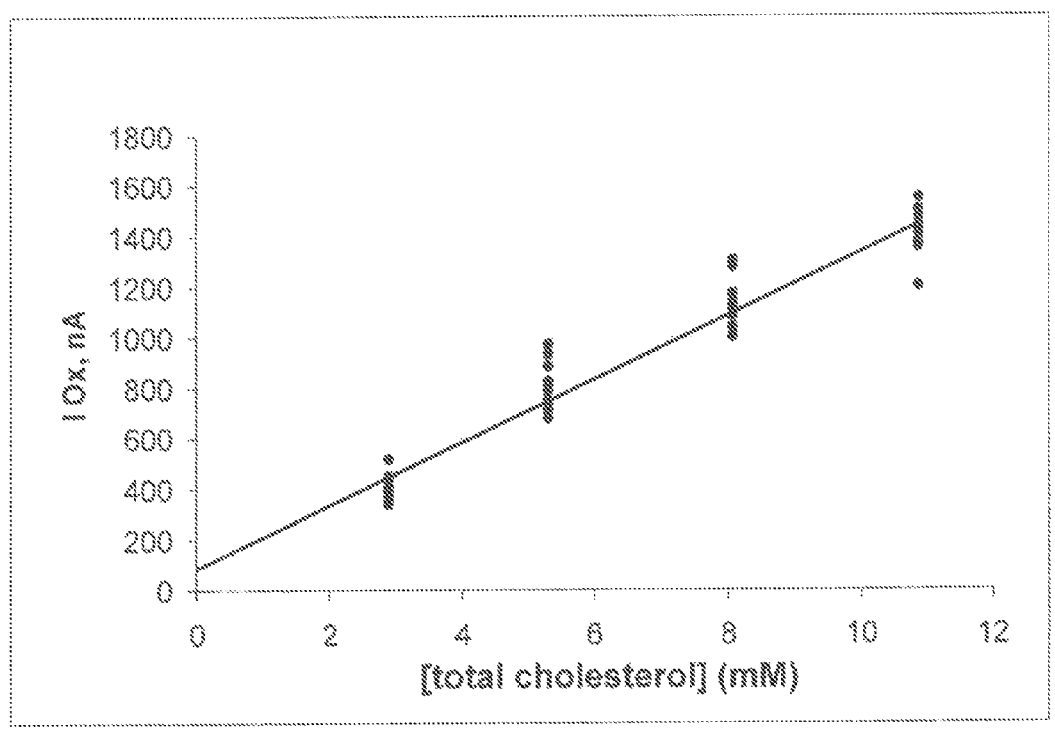
FIG. 6 shows a calibration plot of oxidation current versus the total cholesterol concentration for different human sera samples.

Sensors were tested as detailed in the Standard electrochemical testing protocol given in Example 2. The oxidation current was measured at +0.15V for 1 second at 11 consecutive time intervals, for a period of 140 seconds, followed by a reduction current measured at −0.45V for 1 second. There was a 14 second delay between oxidations which resulted in oxidations at approximately 0, 14, 28, 42, 56, 70, 84, 98, 112, 126 and 140 seconds. Data was analysed for current values at 1 second on the transient. FIG. 6 shows a calibration plot of oxidation current versus the total cholesterol concentration for different human sera samples. Results are shown in Table 5.

TABLE 5

Effect of using different coenzymes in the total cholesterol sensor.

| Coenzyme | Gradient (nA/mM) |
|---|---|
| TNAD | 112 |
| TNADK | 126 |

Example 6

Clinical Trial

The enzyme mix dispensing mixture was prepared as followed. Tris buffer containing MgSO$_4$, glycine, myo-inositol, ectoine, CHAPS, deoxybigCHAP was used to make a solution containing Ru(NH$_3$)$_6$Cl$_3$, TNAD, PdR, ChE and ChDH (gelatine free).

Approximate concentrations in final mix:
0.1 M Tris (pH 9.0)
100 mM MgSO$_4$
5% w/v glycine
1% w/v myo-inositol
1% w/v ectoine
3% w/v CHAPS
3% w/v deoxybigCHAP(DBC)
80 mM Ru(NH$_3$)$_6$Cl$_3$
8.8 mM TNAD
4.2 mg/ml PdR
3.4 mg/ml ChE
66.7 mg/ml ChDH A 0.6 µl aliquot was dispensed per well by hand. Once dispensed the solutions in the sensors were freeze dried. Screen printed sensors had laser drilled wells.

Sensors were tested as detailed in the Standard electrochemical testing protocol given in Example 2.

Figure 7:
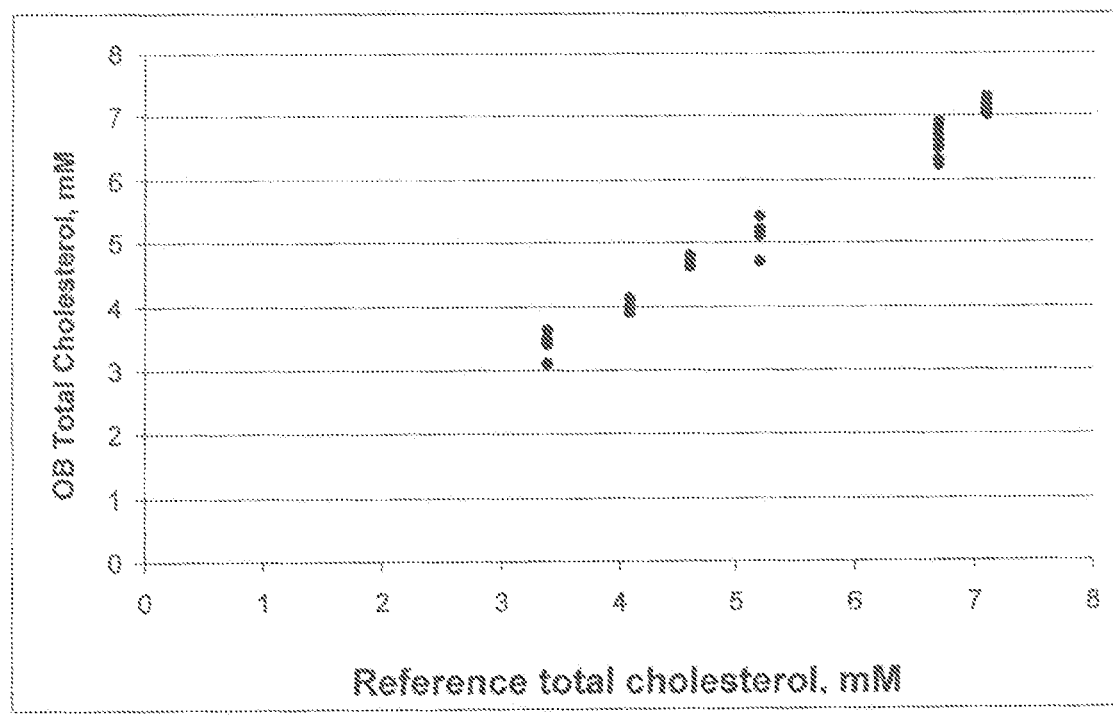
FIG. 7 shows a comparison of total cholesterol concentration obtained using sensors according to the present invention to that measured using typical total cholesterol reference method (Randox).

For comparison with known, clinically used and accredited methods, the same samples were concurrently tested using a Randox Clinical analyser. Results are shown in FIG. 7, which is a comparison of total cholesterol concentration obtained using sensors according to the present invention to that measured using typical total cholesterol reference method (Randox).

Trigyceride Test

Example 7

Freeze Dried Triglyceride Sensors Using Different Bile Salts

Preparation of enzyme mix:
HEPBS buffer containing NH$_4$Cl, glycine, ectoine, surfactant, Ru(NH$_3$)$_6$Cl$_3$ was used to make solutions containing TNAD, diaphorase, lipase, which were subsequently used, along with the aforementioned buffer solution to make a single solution containing GlyDH.

Approximate concentrations in final mix:
0.1M HEPBS (pH 9.0)
10 mM NH$_4$Cl
10% w/v glycine
1% w/v ectoine
1% CHAPS or NaTC
80 mM Ru(NH$_3$)$_6$Cl$_3$
18 mM TNAD
6.6 mg/ml diaphorase
45 mg/ml GlyDH
100 mg/ml lipase A 0.6 µl aliquot of enzyme mix was dispensed per well. Once dispensed the solutions in the sensors were freeze dried. Screen printed sensors had laser drilled wells.

Figure 8:
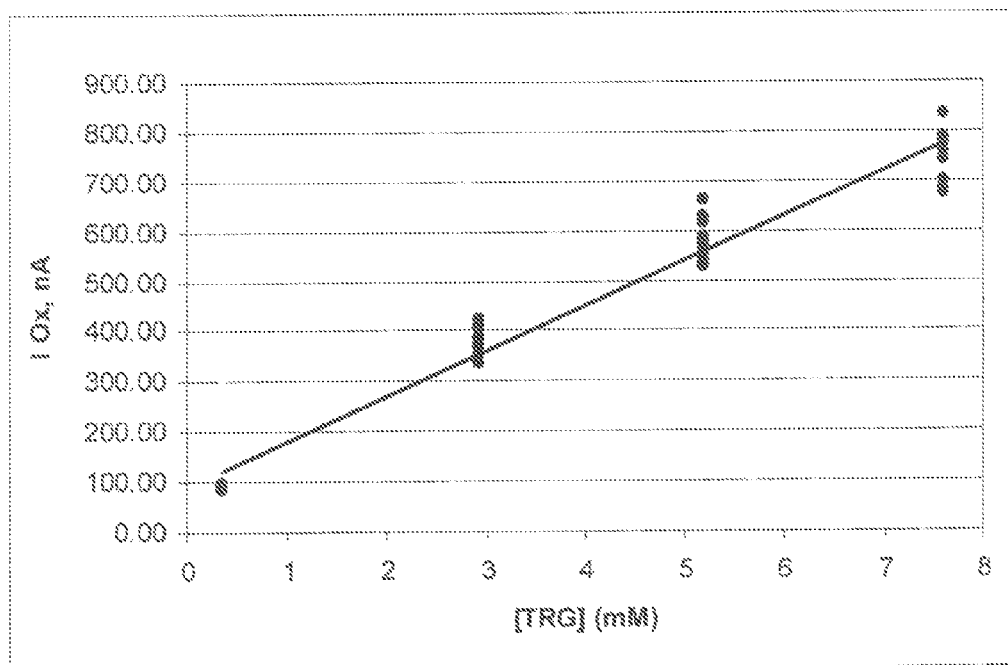
FIG. 8 shows a typical calibration plot of oxidation current versus the triglyceride (TRG) concentration for different human plasma samples using 1% NaTC in the TRG sensor.

Sensors were tested as detailed in the Standard electrochemical testing protocol given in Example 2. A typical calibration plot of oxidation current versus the triglyceride (TRG) concentration for different human plasma samples using 1% NaTC in the TRG sensor is shown in FIG. 8. Results are shown in Table 6.

TABLE 6

Effect of varying bile salt on response of TRG sensor.

| Surfactant | Gradient nA/mM |
|---|---|
| 1% NaTC | 95.1 |
| 1% CHAPS | 92.1 |

Example 8

Spectroscopic Testing Using Varying Concentrations of CHAPS

Several experiments were performed using the same basic enzyme mix, varying the CHAPS concentration used. The basic enzyme mix was prepared as follows:

HEPBS buffer containing NH$_4$Cl, ectoine, varying % w/v CHAPS, was used to make solutions containing potassium ferricyanide and NAD, lipase, diaphorase which were subsequently used, along with the aforementioned buffer solution, to make a single solution containing GlyDH.

Figure 9:
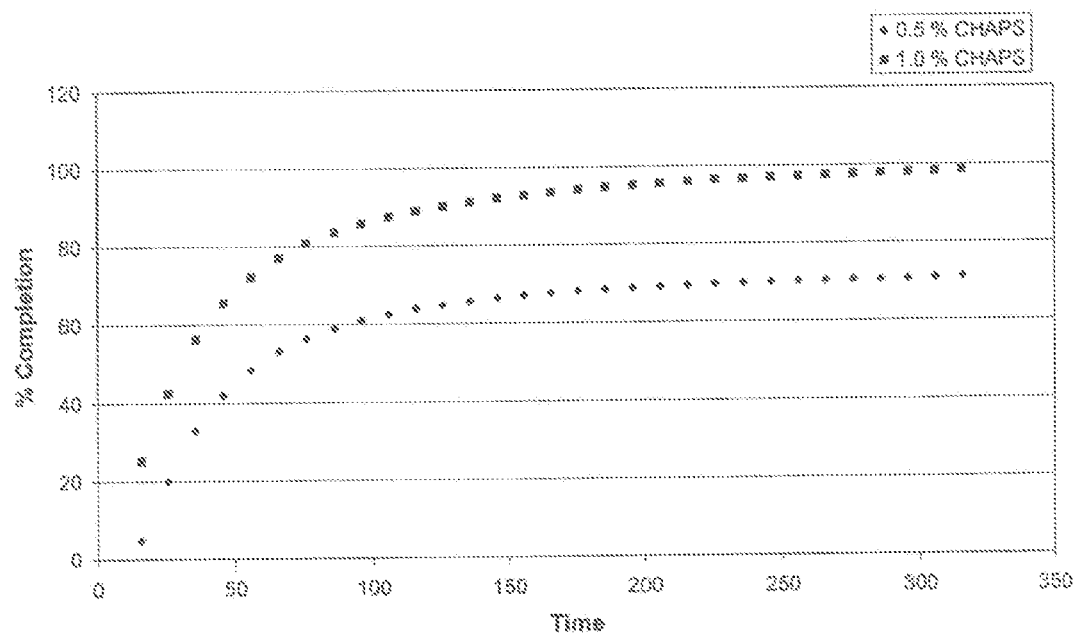
FIG. 9 shows a plot of percentage completion of Triglyceride (TRG) reaction over time with respect to CHAPS concentration.

Approximate concentrations following addition of plasma:
5 mM NH$_4$Cl, 0.05M HEPBS (pH 9.0)
0.5% Ectoine
0.5% or 1% CHAPS
4 mM potassium ferricyanide
1.5 mg/ml NAD
5.6 mg/ml GlyDH
0.8 mg/ml diaphorase
12.5 mg/ml lipase Enzyme mixtures (50 µl each) were tested by the addition of plasma (50 µl). The rate of change of absorption of ferricyanide was measured on a Biotek plate reader at 405 nm, kinetic cycle, 50 repeats with 5 sec time lag between readings. Results are shown in FIG. 9, which is a plot of percentage completion of Triglyceride (TRG) reaction over time with respect to CHAPS concentration.

Example 9

Alternative Redox Agent

The enzyme mix dispensing mixture was prepared as follows. Tris buffer containing glycine, NH$_4$Cl, ectoine, CHAPS was used to make the final solution containing Ru(acac)$_2$(Py-3-CO$_2$H)(Py-3-CO$_2$), TNAD, diaphorase, lipase and GlyDH.

Approximate concentrations in final mix:
0.1M Tris (pH 9.0)
1.4 M glycine
10 mM NH$_4$Cl
73 mM ectoine
1% w/v CHAPS
20 mM Ru(acac)$_2$(Py-3-CO$_2$H)(Py-3-CO$_2$)
22 mM TNAD
8 mg/ml diaphorase
100 mg/ml lipase
54 mg/ml GlyDH A 0.6 µl aliquot of enzyme mix was dispensed per well. Once dispensed the solutions in the sensors were freeze dried. Screen printed sensors had laser drilled wells.

Figure 10:
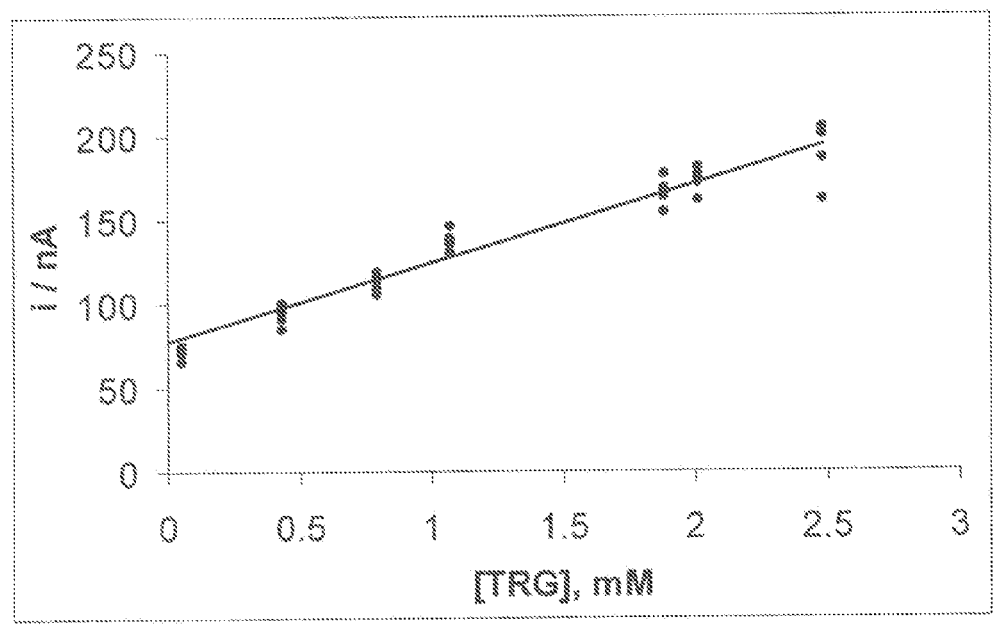
FIG. 10 shows a typical calibration plot of oxidation current versus the triglyceride (TRG) concentration for different human plasma samples using $[Ru(acac)_2(Py-3-CO_2H)(Py-3-CO_2)]$ and 1% CHAPS in the TRG sensor.

Sensors were tested as detailed in the Standard electrochemical testing protocol given in Example 2. FIG. 10 shows a typical calibration plot of oxidation current versus the triglyceride (TRG) concentration for different human plasma samples using [Ru(acac)$_2$(Py-3-CO$_2$H)(Py-3-CO$_2$)] and 1% CHAPS in the TRG sensor. Results are shown in Table 7.

TABLE 7

Effect of changing the redox agent in a triglyceride (TRG) sensor.

| Redox agent | Gradient nA/mM |
| --- | --- |
| Ru(III)(NH3)6 | 92 |
| [Ru(III)(acac)$_2$(Py-3-CO$_2$H)(Py-3-CO$_2$)] | 47 |

Example 10

Coenzyme Derivatives (i) Preparation and Testing of Freeze Dried Triglyceride Sensors Using NAD and NAD Analogues HEPBS buffer was used to make two solutions containing NH$_4$Cl, lactose, Ru(NH$_3$)$_6$Cl$_3$, GlyDH and lipase; NaTC and diaphorase which were subsequently used to make a single solution containing various NAD analogues.

NAD analogues tested:
APAD (acetyl pyridine adenine dinucleotide).
AHD (3-acetyl pyridine hypoxanthine dinucleotide).
NGD (nicotinamide guanine dinucleotide)
NHD (nicotinamide hypoxanthine dinucleotide)
NaAD (nicotinic acid adenine dinucleotide)
NAD.

Approximate concentrations in final mix:
0.1 M HEPBS (pH 9.0)
9 mM NH$_4$Cl
5% w/v lactose
% w/v NaTC
90 mM Ru(NH$_3$)$_6$Cl$_3$
20 mM NAD/NAD analogue
6.6 mg/ml diaphorase
45 mg/ml GlyDH
50 mg/ml lipase A 0.3 µl aliquot of enzyme mix was dispensed per well. The electrode sheets used had punched wells, the cards were freeze dried.

Figure 11:
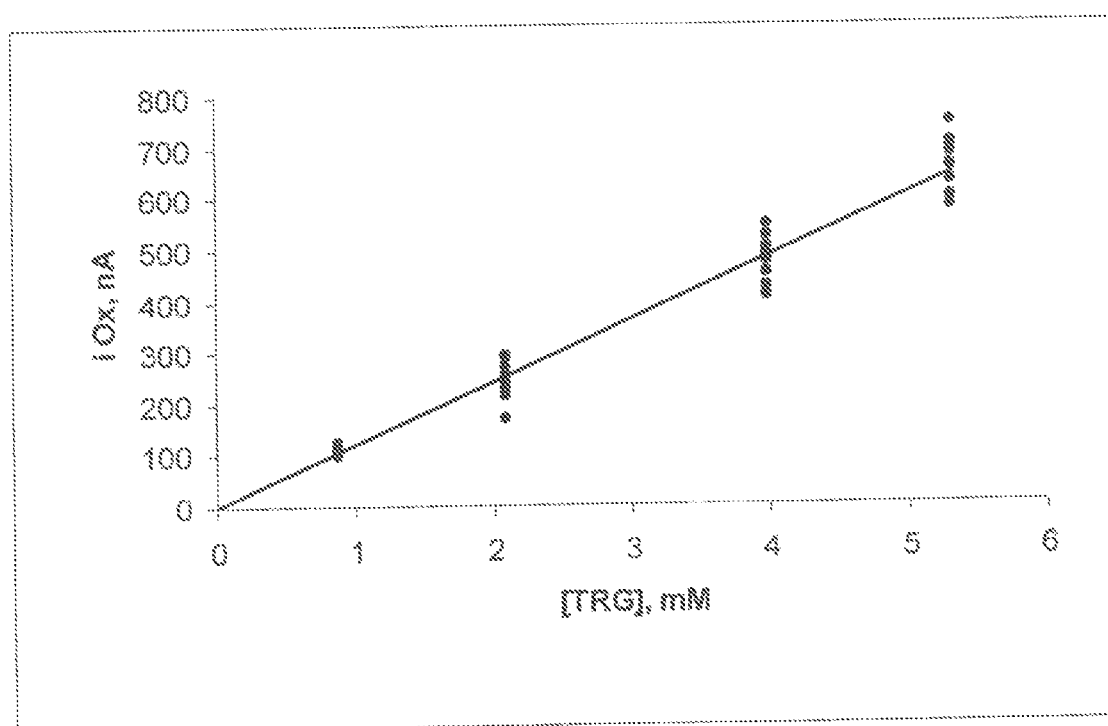
FIG. 11 shows a calibration plot of oxidation current versus the triglyceride (TRG) concentration for different human sera samples using APAD as the cofactor.

Arcare adhesive and Petex spreading membrane were applied to the sensors. Sensors were tested with glycerol solution in water (10 mM). This stock glycerol solution was diluted with water to give 1, 3, 5, 7 and 9 mM glycerol solutions. The volume of sample applied to each sensor using a pipette was 5 µl. The sensors were tested by chronoamperometry using an Autolab (PGSTAT 12) and a multiplexer (MX452, Sternhagen Design). At T=0 seconds the chronoamperometry test was initiated using the multiplexer attached to the Autolab. The oxidation current was measured at +0.15V for 1 second. The data was analysed for current values at 1 second on the transient. FIG. 11 is a calibration plot of oxidation current versus the triglyceride (TRG) concentration for different human sera samples for APAD cofactor. Results are shown in Table 8.

(ii) Use of TNADK

The basic enzyme mix was prepared as follows:
HEPBS buffer containing NH$_4$Cl, KCl, CHAPS, sucrose was used to make two solutions containing, Ru(NH$_3$)$_6$Cl$_3$, diaphorase, lipase, GlyDH; TNADK$^+$ which were subsequently combined to make the final enzyme mix.

Approximate concentrations in final mix:
0.1 M HEPBS (pH 9.0)
10 mM ammonium chloride
9% w/v KCl
1% w/v CHAPS
1% w/v sucrose
80 mM Ru(NH$_3$)$_6$Cl$_3$
17.6 mM TNADK$^+$
6.5 mg/ml diaphorase
100 mg/ml ChE
45 mg/ml GlyDH Sensors were tested as detailed in the Standard electrochemical testing protocol given in Example 2. The oxidation current was measured at +0.15V for 1 second at 11 consecutive time intervals, for a period of 140 seconds, followed by a reduction current measured at −0.45V for 1 second. There was a 14 second delay between oxidations which resulted in oxidations at approximately 0, 14, 28, 42, 56, 70, 84, 98, 112, 126 and 140 seconds. Data was analysed for current values at 1 second on the transient. Results are shown in Table 8.

TABLE 8

Effect of using different co-factors on the triglyceride (TRG) sensor.

| Cofactor | Gradient (nA/mM) |
|---|---|
| APAD | 99 |
| AHD | 4 |
| NaAD | 5 |
| NAD | 151 |
| NHD | 105 |
| NGD | 101 |
| TNADK+ | 121 |

Example 11

Clinical Trial

Figure 12:
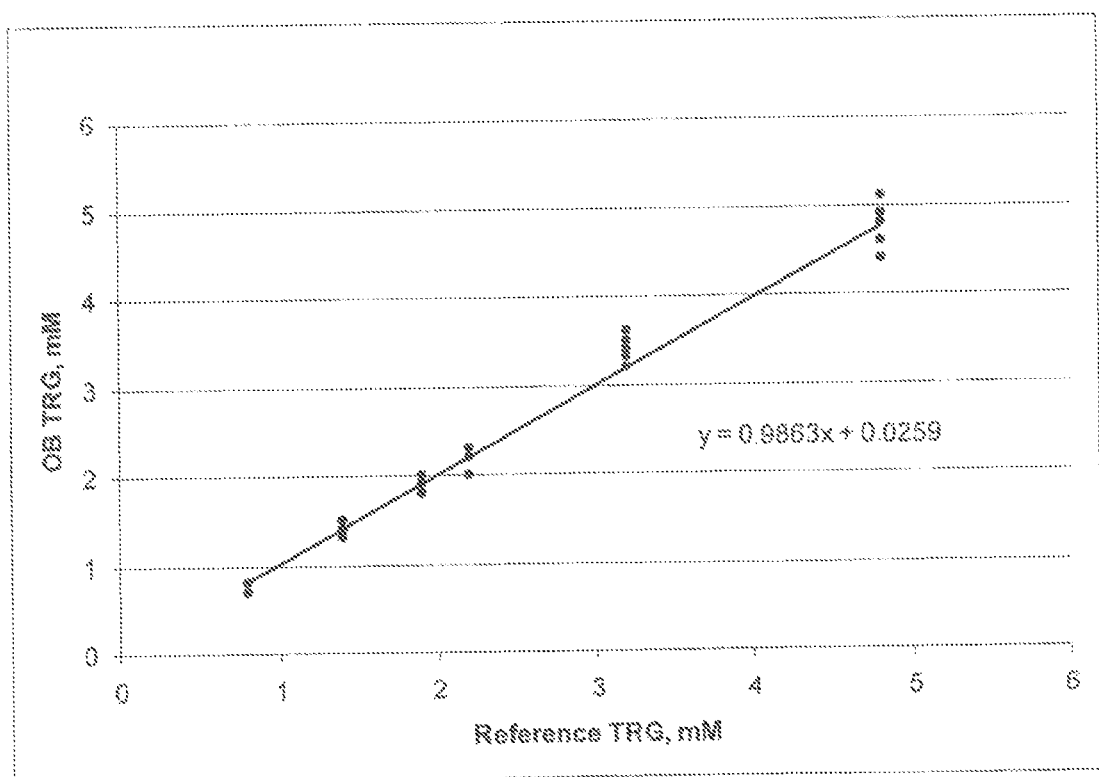
FIG. 12 shows a comparison of triglyceride (TRG) concentration obtained using OB sensors to that measured using typical TRG reference method (Randox).

The enzyme mix dispensing mixture was prepared as followed.
HEPBS buffer containing $NH_4Cl$, KCl, CHAPS, sucrose was used to make a solution containing, $Ru(NH_3)_6Cl_3$, diaphorase, lipase, GlyDH and TNADK+ which was the final enzyme mix.
Approximate concentrations in final mix:
0.1 M HEPBS (pH 9.0)
10 mM ammonium chloride
9% w/v KCl
1% w/v CHAPS
1% w/v sucrose
80 mM $Ru(NH_3)_6Cl_3$
17.6 mM TNADK+
6.5 mg/ml diaphorase
100 mg/ml lipase
45 mg/ml GlyDH
A 0.6 µl aliquot was dispensed per well by hand. Once dispensed the solutions in the sensors were freeze dried. Screen printed sensors had laser drilled wells.
Sensors were tested as detailed in the Standard electrochemical testing protocol given in Example 2, except sensors comprised a flow cell.
For comparison with known, clinically used and accredited methods, the same samples were concurrently tested using a Randox Clinical analyser. Results are shown in FIG. 12, which shows a comparison of triglyceride (TRG) concentration obtained using OB sensors to that measured using typical TRG reference method (Randox).

Example 12

Preparation and Testing of Freeze Dried Triglyceride Sensors Using TNAD and Either Genzyme Lipase or the Standard Toyobo Lipase HEPBS buffer containing $NH_4Cl$, KCl, CHAPS and sucrose was used to make two solutions containing $Ru(NH_3)_6Cl_3$, TNAD, GlyDH and lipase (from either Toyobo or Genzyme). These solutions were subsequently mixed to produce the final enzyme mix solution.
Approximate concentrations in final mix:
0.1 M HEPBS (pH 9.0)
10 mM ammonium chloride
9% w/v KCl
1% w/v CHAPS
1% w/v sucrose
80 mM $Ru(NH_3)_6Cl_3$
17.6 mM TNADK+
6.5 mg/ml diaphorase
100 mg/ml lipase
45 mg/ml GlyDH
A 0.3 µl aliquot of enzyme mix was dispensed per well. Once dispensed the solutions in the well were freeze dried. The electrode sheets used had punched wells.
Arcare adhesive and Petex spreading membrane were applied to the sensors. Sensors were tested with defrosted plasma samples, and also delipidated serum (Scipac). The volume of sample applied to each sensor using a pipette was 5 µl. The sensors were tested by chronoamperometry using a PARSTAT potentiostat and a multiplexer (MX452, Sternhagen Design). At T=0 seconds the chronoamperometry test was initiated using the multiplexer attached to the Autolab. The oxidation current was measured at +0.15V for 1 second, followed by a reduction current measured at −0.45V for 1 second. The data was analysed for current values at 1 second on the transient. Results are shown in Table 9.

TABLE 9

Effect of different lipases on the triglyceride (TRG) sensor.

| Cofactor | Gradient (nA/mM) |
|---|---|
| Toyobo Lipase | 123.1 |
| Genzyme Lipase | 158.7 |

Example 13

(i) Diaphorase Vs. PdR Electrochemical

Figure 13:
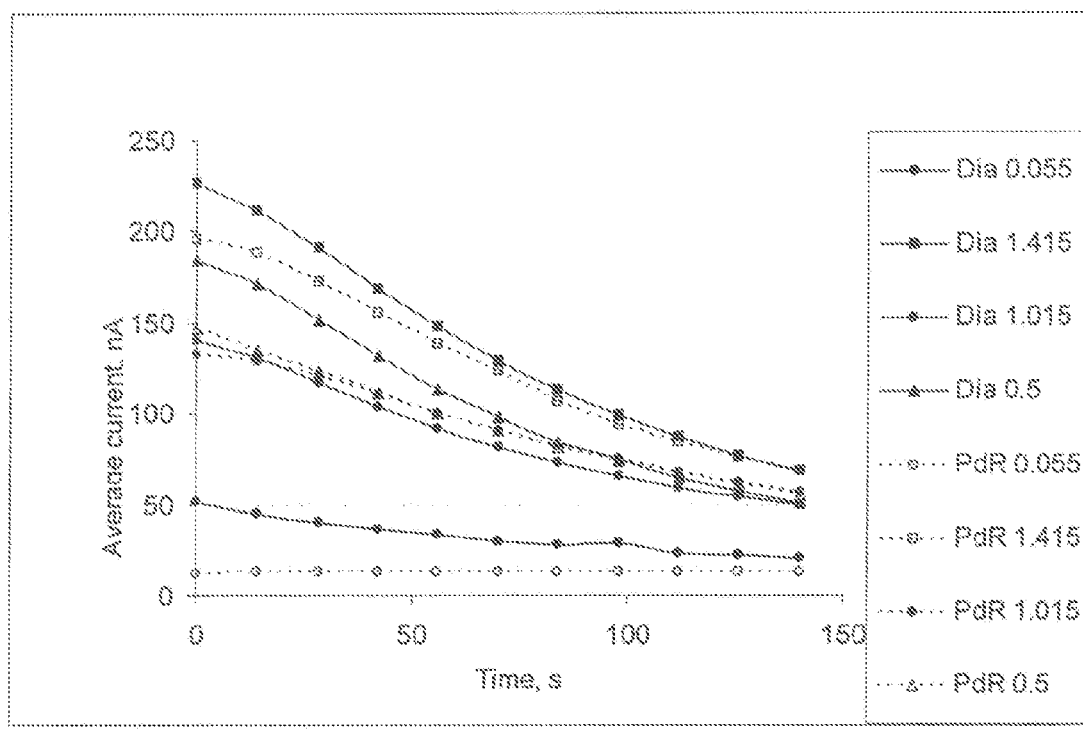
FIG. 13 shows average currents of solutions with diaphorase (Dia) or PdR. The numbers following Dia or PdR refer to the TRG concentration of the plasma sample.

Several experiments were performed using the same basic enzyme mix using either PdR or diphorase. The basic enzyme mix was prepared as follows:
HEPBS buffer containing $NH_4Cl$, KCl sucrose and CHAPS was used to make solutions containing, NAD and ferricyanide; GlyDH; PdR or diaphorase. These solutions were subsequently added, along with the buffer solution, to lipase to produce the final enzyme mix.
The mixes were dispensed onto electrodes 'in the wet'.
The enzyme mix was tested by addition of plasma.
Approximate concentrations following addition of plasma:
5 mM $NH_4Cl$, 0.05M HEPBS (pH 9.0)
4.5% w/v KCl
0.5% w/v Sucrose
0.5% w/v CHAPS
40 mM Ruthenium Hexaamine
6 mg/ml NAD
22.5 mg/ml GlyDH
3.3 mg/ml diaphorase or PdR
50 mg/ml lipase
Sensors were tested as detailed in the Standard electrochemical testing protocol given in Example 2, except that the oxidation current was measured at +0.15V for 1 second at 14 second consecutive time intervals, for a period of 140 seconds. There was a 14 second delay between oxidations which resulted in oxidations at approximately 0, 14, 28, 42, 56, 70, 84, 98, 112, 126 and 140 seconds. Data was analysed for current values at 1 second on the transient. Results are shown in FIG. 13, which shows average currents of solutions with diaphorase (Dia) or PdR. The numbers following Dia or PdR refer to the TRG concentration of the plasma sample.

(ii) Diaphorase/PdR Spectrophotometric

Several experiments were performed using the same basic enzyme mix, using either diaphorase or PdR. The basic enzyme mix was prepared as follows:

HEPBS buffer containing $NH_4Cl$ and CHAPS was used to make solutions containing, NAD and ferricyanide; GlyDH; PdR or diaphorase. These solutions were subsequently added, along with the buffer solution, to lipase or esterase to produce the final enzyme mix.

Figure 14:
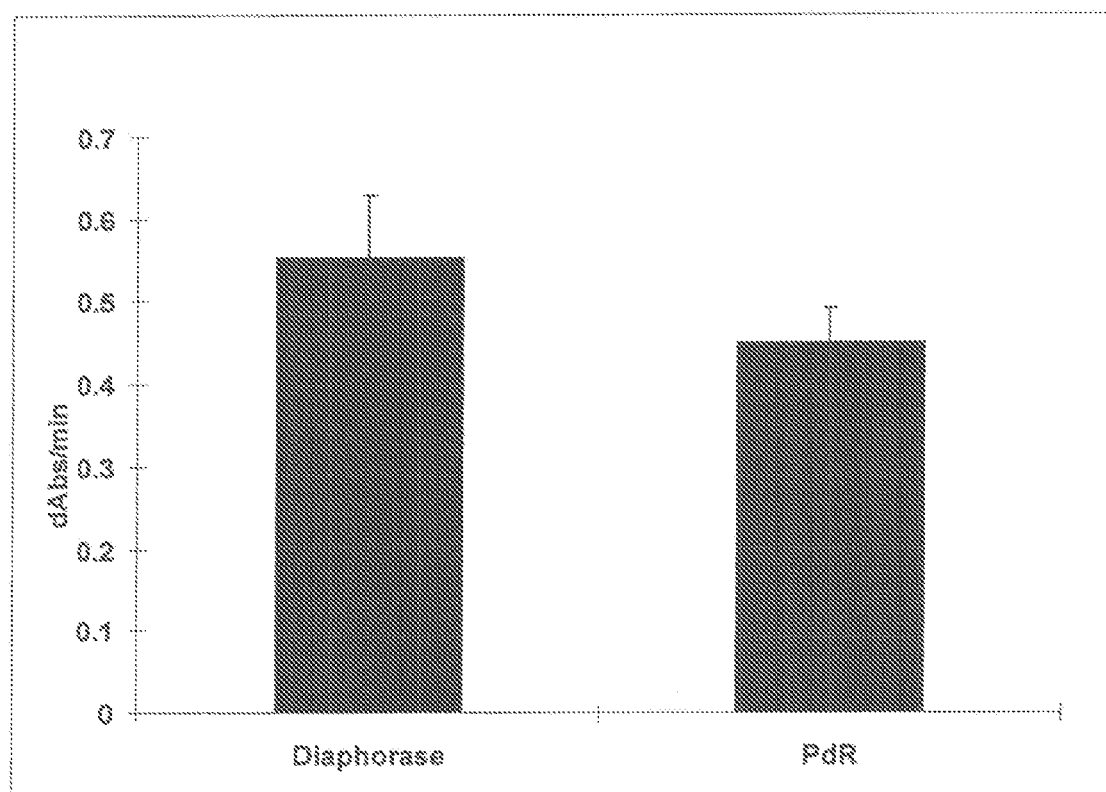
FIG. 14 shows results of initial rates of change of absorption (+/−SD) of ferricyanide for the first 30 sec of reaction with diaphorase or PdR.

Approximate concentrations following addition of plasma:
5 mM $NH_4Cl$, 0.05M HEPBS (pH 9.0)
0.5% CHAPS
4 mM potassium ferricyanide
1.5 mg/ml NAD
5.6 mg/ml GlyDH
0.8 mg/ml diaphorase or PdR
12.5 mg/ml lipase or esterase Enzyme mixtures (50 μl each) were tested by the addition of plasma (50 μl). The rate of change of absorption of ferricyanide was measured on Biotek plate reader at 405 nm, kinetic cycle, 50 repeats with 5 sec time lag between readings. Results of initial rates of change of absorption (+/−SD) of ferricyanide for the first 30 sec of reaction with diaphorase or PdR are shown in FIG. 14.

The invention has been described with reference to various specific embodiments and examples. However, it is to be understood that the invention is in no way limited to these specific embodiments and examples.

The invention claimed is:

1. An electrochemical method for the determination of the amount of triglyceride in a sample, said method comprising reacting the sample with a reagent mixture comprising
   (a2) a surfactant comprising one or more bile acid derivatives or salts thereof;
   (b2) a triglyceride hydrolysing reagent;
   (c2) glycerol dehydrogenase;
   (d2) a coenzyme; and
   (e2) a redox agent capable of being oxidised or reduced to form a product;
and electrochemically detecting the amount of product formed.

2. A method according to claim 1, further comprising determining the total cholesterol content of the sample, said determining comprising further reacting the sample with a further series of reagents comprising:
   (a1) a surfactant comprising one or more bile acid derivatives or salts thereof;
   (b1) a cholesterol ester hydrolysing reagent;
   (c1) cholesterol dehydrogenase;
   (d1) a coenzyme; and
   (e1) a redox agent capable of being oxidised or reduced to form a second product, and electrochemically detecting the amount of said second product formed.

3. A method according to claim 1 wherein the triglyceride hydrolysing reagent (b1) comprises a lipoprotein lipase.

4. A method according to claim 1, wherein the reagent mixture additionally comprises a reductase.

5. A method according to claim 4, wherein the reductase comprises diaphorase or putidaredoxin reductase.

6. A method according to claim 1, wherein the coenzyme (d2) comprises TNAD.

7. A method according to claim 1, wherein the redox agent (e2) comprises one of $Fe(CN)_6^{3-}$, $Ru(NH_3)_6^{3+}$, $Ru(acac)_2(Py\text{-}3\text{-}CO_2H)(Py\text{-}3\text{-}CO_2)$, and ferrocenium monocarboxylic acid (FMCA).

8. A method according to claim 1, wherein the step of electrochemically detecting the amount of product formed comprises applying a potential across the sample, and measuring the resulting electrochemical response to the applied potential.

9. A method according to claim 1, wherein the reagent mixture is provided in an electrochemical cell having at least two electrodes, the method further comprising providing the electrochemical cell, and contacting the sample with the reagent mixture and the at least two electrodes by applying the sample to the electrochemical cell; wherein the step of electrochemically detecting the amount of product formed comprises applying a potential across the at least two electrodes, and measuring the resulting electrochemical response.

10. A method according to claim 1, wherein the sample comprises whole blood and wherein the method additionally comprises the step of filtering the sample to remove red blood cells.

11. A reagent mixture for use in an electrochemical method for the determination of the amount of triglyceride in a sample, the reagent mixture comprising
   (a2) a surfactant comprising one or more bile acid derivatives or salts thereof;
   (b2) a triglyceride hydrolysing reagent;
   (c2) glycerol dehydrogenase;
   (d2) a coenzyme; and
   (e2) a redox agent capable of being oxidised or reduced to form a product.

12. A reagent mixture according to claim 11 further comprising (f2) a reductase.

13. A reagent mixture according to claim 12 wherein the reductase comprises diaphorase or putidaredoxin reductase.

14. A reagent mixture according to claim 11 wherein the coenzyme (d2) comprises TNAD.

15. A reagent mixture according to claim 11 wherein the redox agent (e2) comprises one of $Fe(CN)_6^{3-}$, $Ru(NH_3)_6^{3+}$, $Ru(acac)_2(Py\text{-}3\text{-}CO_2H)(Py\text{-}3\text{-}CO_2)$, and ferrocenium monocarboxylic acid (FMCA).

16. A kit for measuring the triglyceride content of a sample, the kit comprising
   one or more electrochemical cells, each cell having a working electrode, a reference or pseudo reference electrode and optionally a separate counter electrode;
   a reagent mixture comprising:
      (a2) a surfactant comprising one or more bile acid derivatives or salts thereof;
      (b2) a triglyceride hydrolysing reagent;
      (c2) glycerol dehydrogenase;
      (d2) a coenzyme; and
      (e2) a redox agent capable of being oxidised or reduced to form a product, said reagent mixture being associated with one of said electrochemical cells;
   a power supply for applying a potential across each cell; and
   a measuring instrument for measuring the resulting electrochemical response of each cell.

17. A kit according to claim 16 for measuring the total cholesterol and triglyceride content of a sample, which kit comprises two or more electrochemical cells and a further series of reagents associated with one of said electrochemical cells, the further series of reagents comprising:

(a1) a surfactant comprising one or more bile acid derivatives or salts thereof;
(b1) a cholesterol ester hydrolysing reagent;
(c1) cholesterol dehydrogenase;
(d1) a coenzyme; and
(e1) a redox agent capable of being oxidised or reduced to form a product.

18. A kit according to claim 16, wherein the working electrode of the or each electrochemical cell is a microelectrode having at least one dimension of less than 50 μm.

19. A method of breaking down the lipoprotein structure of a sample comprising lipoproteins by using one or more bile acid derivatives or salts thereof as a surfactant, in an electrochemical method for the determination of the amount of triglyceride in a sample, said method comprising reacting the sample with a reagent mixture comprising
(a2) said one or more bile acid derivatives or salts thereof;
(b2) a triglyceride hydrolysing reagent;
(c2) glycerol dehydrogenase;
(d2) a coenzyme; and
(e2) a redox agent capable of being oxidised or reduced to form a product;
and electrochemically detecting the amount of product formed.

20. A method comprising:
providing a liquid sample containing an amount of triglycerides, said triglycerides being bound to lipoproteins;
providing a reagent mixture comprising
(a2) a surfactant comprising one or more bile acid derivatives or salts thereof;
(b2) a triglyceride hydrolysing reagent;
(c2) glycerol dehydrogenase;
(d2) a coenzyme; and
(e2) a redox agent capable of being oxidised or reduced to form a product;
freeing the triglycerides from the lipoproteins within the liquid sample by contacting the triglycerides with said surfactant comprising bile acid derivatives or salts thereof, said surfactant being configured to break the lipoproteins from the triglycerides;
breaking down the freed triglycerides produced within the liquid sample into a proportionate amount of glycerol by reacting the freed triglycerides with said triglyceride hydrolyzing reagent; and
electrochemically determining the amount of glycerol in the liquid sample by:
reacting the glycerol with said glycerol dehydrogenase and said coenzyme in the presence of said redox agent;
applying an electrical potential to the liquid sample;
measuring the resulting electrochemical response; and
correlating the measured response to the amount of glycerol;
wherein the method provides an indication of the total triglyceride content of the liquid sample.

\* \* \* \* \*